(12) United States Patent
Murata

(10) Patent No.: US 6,348,923 B2
(45) Date of Patent: Feb. 19, 2002

(54) OBJECT IMAGE DISPLAY DEVICES

(75) Inventor: Yoshiyuki Murata, Ome (JP)

(73) Assignee: Casio Computer Co., Ltd., Tokyo (JP)

(*) Notice: Subject to any disclaimer, the term of this patent is extended or adjusted under 35 U.S.C. 154(b) by 13 days.

(21) Appl. No.: 09/095,870

(22) Filed: Jun. 11, 1998

Related U.S. Application Data

(62) Division of application No. 08/742,336, filed on Nov. 1, 1996, which is a division of application No. 08/172,120, filed on Dec. 22, 1993, now Pat. No. 5,638,502.

(30) Foreign Application Priority Data

Dec. 25, 1992 (JP) ............................................. 4-358314
Dec. 30, 1992 (JP) ............................................. 4-359848
Dec. 30, 1992 (JP) ............................................. 4-360167

(51) Int. Cl.⁷ ............................................. G06T 15/00
(52) U.S. Cl. ............................................. 345/435
(58) Field of Search ............................... 345/435, 473, 345/474, 475, 113, 114

(56) References Cited

U.S. PATENT DOCUMENTS

| | | | |
|---|---|---|---|
| 2,150,853 A | 3/1939 | Warren et al. | 392/322 |
| 4,149,246 A | 4/1979 | Goldman | 700/132 |
| 4,276,570 A | 6/1981 | Burson et al. | 382/276 |
| 4,602,280 A | 7/1986 | Maloomian | 358/93 |
| 4,839,822 A | 6/1989 | Dormond et al. | 706/45 |
| 5,057,019 A | 10/1991 | Harvey | 434/155 |
| 5,060,171 A | 10/1991 | Steir et al. | 345/435 |
| 5,067,087 A | 11/1991 | Seki et al. | 700/182 |
| 5,179,642 A | 1/1993 | Komatsu | 345/435 |
| 5,247,610 A | 9/1993 | Oshima et al. | 345/435 |
| 5,267,154 A | 11/1993 | Takeuchi et al. | 345/435 |
| 5,280,570 A | 1/1994 | Jordan | 345/473 |
| 5,487,140 A | 1/1996 | Toya | 345/435 |
| 5,491,777 A | 2/1996 | Mase et al. | 345/433 |
| 5,537,662 A | 7/1996 | Sato | 707/1 |
| 5,568,599 A | 10/1996 | Yoshino et al. | 345/435 |
| 5,714,977 A * | 2/1998 | McNeil | 345/473 |

FOREIGN PATENT DOCUMENTS

| | | |
|---|---|---|
| EP | 0211345 A3 | 2/1987 |
| EP | 0241071 A1 | 10/1987 |
| EP | 0275124 | 7/1988 |
| EP | 0387827 A3 | 9/1990 |
| EP | 0485766 A3 | 5/1992 |
| EP | 0584759 A2 | 3/1994 |
| GB | 1546072 | 5/1979 |
| GB | 1605135 | 1/1982 |
| JP | 3-129572 | 6/1991 |
| WO | WO 80/02490 | 11/1980 |

OTHER PUBLICATIONS

Eleventh Annual International Phoenix Conference On Computers And Communications, Apr. 1–3, 1992; Scottsdale, Arizona, USA, pp. 525–530 XP 302613, Curtis et al, "XFACE, An X Tool Presenting Multivariable Data, And Its Use With Software Metrics".

Eurographics '91, Proceedings Of The European Computer Graphics Conference And Exhibition, Sep. 2–6, 1991, Vienna, Austria, pp. 33–45, Patel et al, "Faces: Facial Animation Construction and Editing System".

* cited by examiner

*Primary Examiner*—Phu K. Nguyen
(74) *Attorney, Agent, or Firm*—Frishauf, Holtz, Goodman, Langer & Chick, P.C.

(57) ABSTRACT

A device for the creating and displaying an object image. A plurality of object images is created on the basis of a combination of part patterns on the respective parts of an object. A different object image related to the respective object images is synthesized from the purality of created object images and displayed. An object image is created and displayed automatically which has a different shape imagined when the weight, height and intake calory of the created object image is increase/decreased. When a front object image is created, parts patterns for an object image on a different view corresponding to the front object image are designated and combined to create an object image on a different view.

78 Claims, 38 Drawing Sheets

FIG.4
BASIC PART PATTERN ROM 12B
| PART \ NO. | 01 | 02 | | 50 |
|---|---|---|---|---|
| 1 CONTOUR |  |  | |  |
| 2 HAIR STYLE | 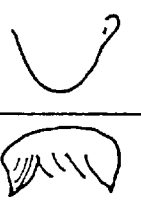 |  | | 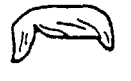 |
| 3 EYES |  |  | |  |
| ... | | | | |
| 10 BOTH LEGS |  |  | |  |

FIG.5

INFANT PART PATTERN ROM

| PART \ NO. | 01 | 02 | 03 | | 50 |
|---|---|---|---|---|---|
| 1 CONTOUR | ∪ | ∪ | ∪ | | ∪ |
| 2 HAIR STYLE | | | | | |
| 3 DRESS | | | | | |
| 5 LEGS | | | | | |

FIG.6

DISPLAY REGISTER — 13

| DATA ITEM | INDIVIDUAL DATA AREA ||||| MONTAGE DATA AREA |||||||||
|---|---|---|---|---|---|---|---|---|---|---|---|---|---|
| | NAME | BLOOD | TEL | AGE | CON-TOUR | HAIR STYLE | EYES | NOSE | MOUTH | BROWS | EARS | DRESS | HANDS | LEGS |
| 1 | A | OO | OO | 40 | 01 | 02 | 02 | 05 | ㉚ | 04 | 01 | 03 | NONE | NONE |
| 2 | B | OO | OO | 30 | 50 | 50 | ㊵ | ⑳ | 04 | ③ | ④ | 05 | NONE | NONE |
| 3 | C | OO | OO | 15 | 10 | 11 | 38 | 03 | 04 | 15 | 18 | 20 | 30 | 25 |
| 4 | D | OO | OO | 20 | 5 | 4 | 39 | 05 | 08 | 10 | 11 | 10 | 15 | 14 |
| 50 | H | OO | OO | 50 | 10 | 15 | 09 | 10 | 14 | 20 | 15 | 12 | 15 | 20 |
| INFANT | X | OO | — | 3 | ㊼ | ① | NONE | NONE | NONE | NONE | NONE | ① | ㊵ | ㉚ |
| SELECT PART | 1ST OBJECT | | | | 1 | 1 | 0 | 0 | 1 | 0 | 0 | 1 | 1 | 0 |
| | 2ND OBJECT | | | | 0 | 0 | 1 | 1 | 0 | 1 | 1 | 0 | 0 | 1 |

134 — INDIVIDUAL DATA AREA
135 — MONTAGE DATA AREA
131 — DATA COMBINING AREA
132 — MONTAGE SYNTHESIS AREA
133 — REDUCTION SYNTHESIS AREA
136 — SELECT PART
138 — 1ST OBJECT
137 — 2ND OBJECT
152, 130, 139

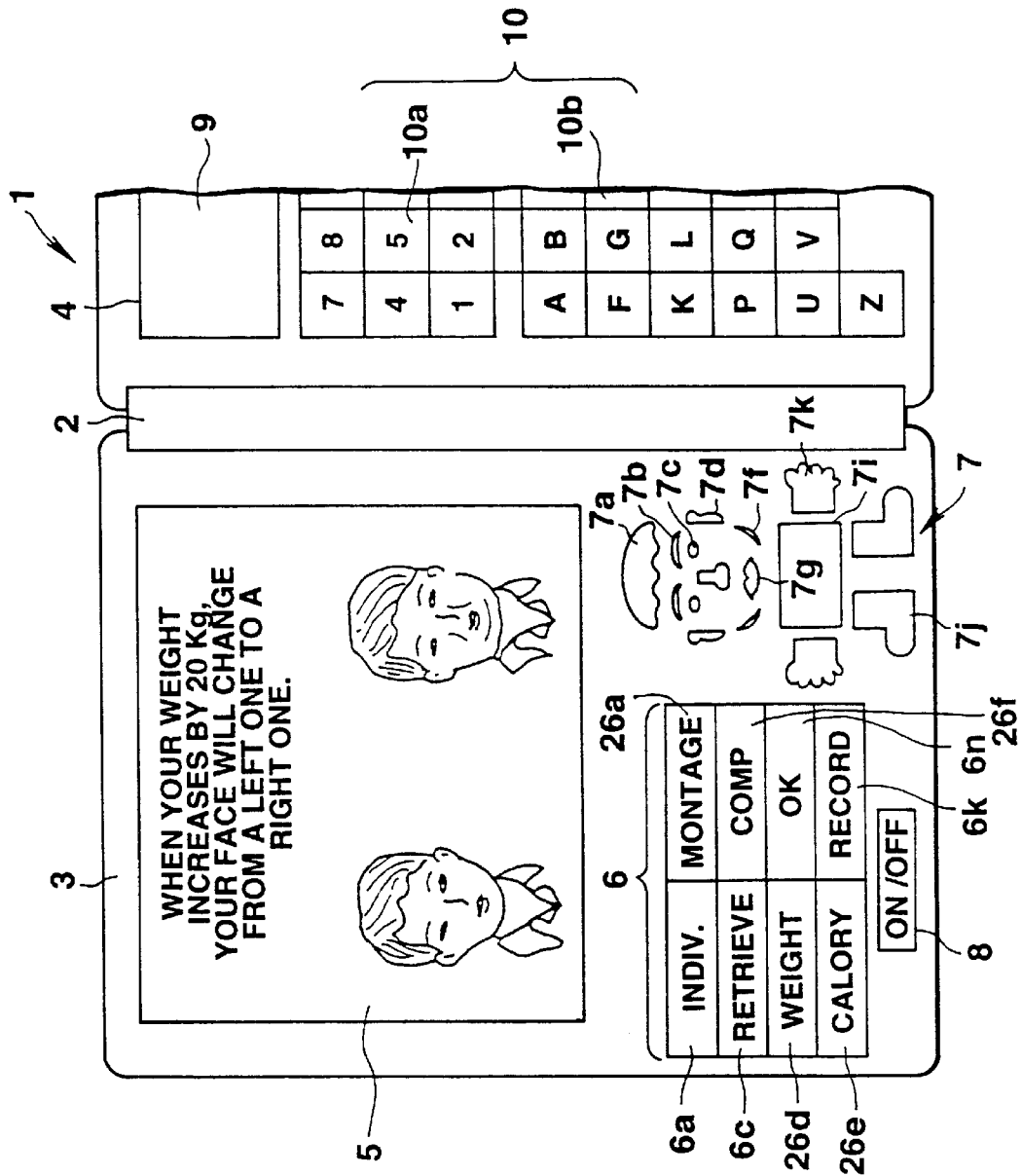

FIG.19

BASIC PART PATTERN ROM

12B

| PART \ NO. | 01 | | 50 |
|---|---|---|---|
| 1 CONTOUR | | | |
| 2 HAIR STYLE | | | |
| 3 EYES | | | |
| 4 NOSE | | | |

FIG.20
WEIGHT INCREASE/DECREASE PART PATTERN ROM 12D
| WEIGHT CHANGE \ NO. | 01 | ... | 50 |
|---|---|---|---|
| +20Kg | (01+20)  | ... | (50+20)  |
| +5Kg | (01+5)  | ... | (50+20)  |
| 0Kg | (01)  | ... | (20)  |
| -20Kg | (01-20) 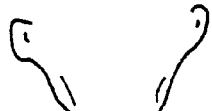 | ... | (50-20) 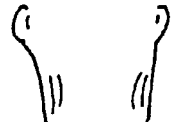 |

FIG.21

INDIVIDUAL/MONTAGE DATA RAM 13A

DISPLAY REGISTER 130

INDIVIDUAL DATA AREA (134) / MONTAGE DATA AREA (135)

| DATA ITEM | NAME | AD-DRESS | WEIGHT | WEIGHT MEASURE DATE | HEIGHT | HEIGHT MEASURE DATE | | CON-TOUR | HAIR STYLE | EYES | LEGS |
|---|---|---|---|---|---|---|---|---|---|---|---|
| 1 | A | OO | 50 | 1992.12.20 | 170 | 1992.12.20 | OOO | 01 | 01 | 03 | NONE |
| 2 | B | OO | 45 | 1992.10.10 | 168 | 1992.10.10 | OOO | 03 | 04 | 05 | NONE |
| 3 | C | OO | 48 | 1991.10.1 | 170 | 1991.10.1 | OOO | 15 | 18 | 20 | 25 |
| 4 | D | OO | 80 | 1998.8.10 | 189 | 1998.8.10 | OOO | 10 | 11 | 10 | 14 |
| ... | | | | | | | | | | | |
| 50 | H | OO | 90 | 1990.10.10 | 190 | 1990.10.10 | OOO | 20 | 15 | 12 | 20 |
| WEIGHT CHANGE | | | 1 (+20) | 2 (-10) | 3 (+20) | ... | 50 (+10) | | | | |
| CALORY CHANGE | | | 1 (+100) | 2 (+50) | 3 (+60) | ... | 50 (-100) | | | | |

152 / 153 / 154

MONTAGE DATA AREA FOR CALORY CHANGE (155)

| | CON-TOUR | HAIR STYLE | EYES | LEGS |
|---|---|---|---|---|
| | 01 +20 | 01 | 03 | NONE |

MONTAGE DATA AREA FOR WEIGHT CHANGE (156)

| | CON-TOUR | HAIR STYLE | EYES | LEGS |
|---|---|---|---|---|
| | 01 +20 | 01 | 03 | NONE |

WHEN RECORDED

WHEN WEIGHT INCREASES

WHEN WEIGHT DECREASES

FIG.30

BASIC PART PATTERN ROM

| PATTERN NO. / PART | | A (FRONT) | A-1 (RIGHT SIDE) | A-2 (RIGHT SIDE) | | B (FRONT) | B-1 (RIGHT SIDE) | | C-20 (BACK) |
|---|---|---|---|---|---|---|---|---|---|
| 1 | CONTOUR | | | | | | | | |
| 2 | HAIR STYLE | | | | | | | | |
| ⋮ | | | | | | | | | |
| 10 | LEGS | | | | | | | | |

WHEN SET INITIALLY

WHEN RECORD (FRONT)

WHEN DISPLAY (RIGHT SIDE)

WHEN LUMP DISPLAY

OBJECT IMAGE DISPLAY DEVICES

This application is a Div of Ser. No. 08/742,336 filed Nov. 1, 1996, which is an Div of Ser. No. 08/172,120 filed Dec. 22, 1993 U.S. Pat. No. 5,638,502.

BACKGROUND OF THE INVENTION

The present invention relates to object image displaying devices which create and display an object image such as an animal or building.

Conventionally, a so-called object image creating device is known which creates an image of an object such as a face in a manner similar to creation of a montage photograph. This device is provided with a part pattern memory which stores a plurality of data items on part patterns of respective parts of a face such as a "contour", "hair style", "eyes", "nose", "mouth", and "brows". It also provided with a switch which is operated to designate the respective parts of an image and a switch which is operated to designate desired ones of kinds of part patterns related to the parts designated by the part designating switch when the object image is created.

In this case, in order to create any object image, first, the part designating switch is operated to designate parts of the object image. Desired part patterns are selected from among kinds of part patterns stored in the part pattern memory for the respective parts designated by the operation of the part designating switch, and an image of a desired object is created by combining the selected part patterns.

As described above, the conventional object image creating device only creates an object image of composed of a plurality of part patterns and displays that object image created. It, however, cannot rapidly and easily create a different image related to the created object image, for example, a child's face image related to a created husband's face image and a created wife's face image, a person's possible face or whole body image imagined when his current created weight is increased/decreased, or whole body image obtained when his current created weight is increased/decreased, or another side face image related to a created front face image.

SUMMARY OF THE INVENTION

It is therefore an object of the present invention to provide an object image display device which rapidly and easily creates and displays an object image which is related to a created object image.

In order to achieve the above object, according to the present invention, there is provided an object image display device comprising:
part pattern storage means for storing a plurality of kinds of part patterns of each of parts which constitute an object image;
first object image storage means for storing a plurality of first object images each composed of a combination of part patterns selected from among the plurality of kinds of part patterns stored in said part pattern storage means;
part pattern selecting means for selecting one part pattern for each part from among the part patterns which constitute each of the plurality of first object images stored in the first object storage means;
creation means for creating a second object image by combining the part patterns of the respective parts selected by the part pattern selecting means; and
display means for displaying the second object image created by the creation means.

According to another aspect of the present invention, there is provided an object image display device comprising:
image data storage means for storing data on a first and a second image of the same object different in size;
display means for displaying data on the first and second images stored in the image data storage means;
third image data creating means for creating data on a third image having a shape different from the first and second images of the same object as that mentioned above and related to the first and second image data on the basis of the first and second image data stored in the image data storage means; and
display controlling means for controlling the display of the third image data created by the third image data creating means on said display means.

The "same object" points out an object having the same number of identical parts, and includes a human being and a human being, a human being and an animal, and a car and a car.

According to another aspect of the present invention, therer is provided an image display device comprising:
part pattern storage means for storing a plurality of kinds of patterns of parts which constitute at lest a portion of a human body;
first image creating means for creating an image composed of a combination of part patterns for the respective parts selected from among the plurality of part patterns stored in the part pattern storage means;
changed data setting means for setting as changed data on a human body a change in the image created by the first image creating means;
second image creating means for changing at lest one part pattern of a first image created by said first creating means in accordance with changed data set by said change data setting means to a further part pattern stored in said part pattern storage means to create a second image having a shape different from the first image; and
display means for displaying the second image created by the second image creating means.

The "changed data" points out data on a least one of weight and height.

According to a further aspect of the present invention, there is provided an object image display device comprising:
part pattern storage means for storing a plurality of kinds of part patterns for the respective parts which constitute each view of an object image;
part pattern selecting means for selecting part patterns on any view for the respective parts from among the plurality of kinds of part patterns stored in the part pattern storage means;
first object image storage means for storing a first object image on one view composed of a combination of parts patterns for the respective parts designated by the part pattern designating means;
part pattern designating means for designating part patterns for the respective parts of a further view from among the plurality of kinds of part patterns stored in said part pattern storage means in correspondence to the part pattern which constitute the first object image on the one view stored in the first object image storage means;
second object storage means for storing a second image composed of a combination of part patterns for the respective parts of the further view designated by said part pattern designated means; and display means for displaying the second object image on the further view stored in said second object image storage means.

BRIEF DESCRIPTION OF THE DRAWINGS

FIG. 4 shows a stored state of part patterns in a basic part pattern ROM.

FIG. 5 shows a stored state of part patterns in an infant part pattern ROM.

FIG. 6 shows a stored state of data in an individual/montage data RAM.

FIG. 17 is a plan view of an object image display device as a second embodiment of the present invention.

FIG. 19 shows a stored state of part patterns in a basic part pattern ROM.

FIG. 20 shows a stored state of part patterns in a weight increase/decrease part pattern ROM.

FIG. 21 shows a stored state of data in an individual/montage data RAM.

FIG. 30 shows a stored state of part patterns in a basic part pattern ROM.

DETAILED DESCRIPTION

Embodiments of the present invention will be described below with reference to the accompanying drawings.

FIRST EMBODIMENT

Figure 1:
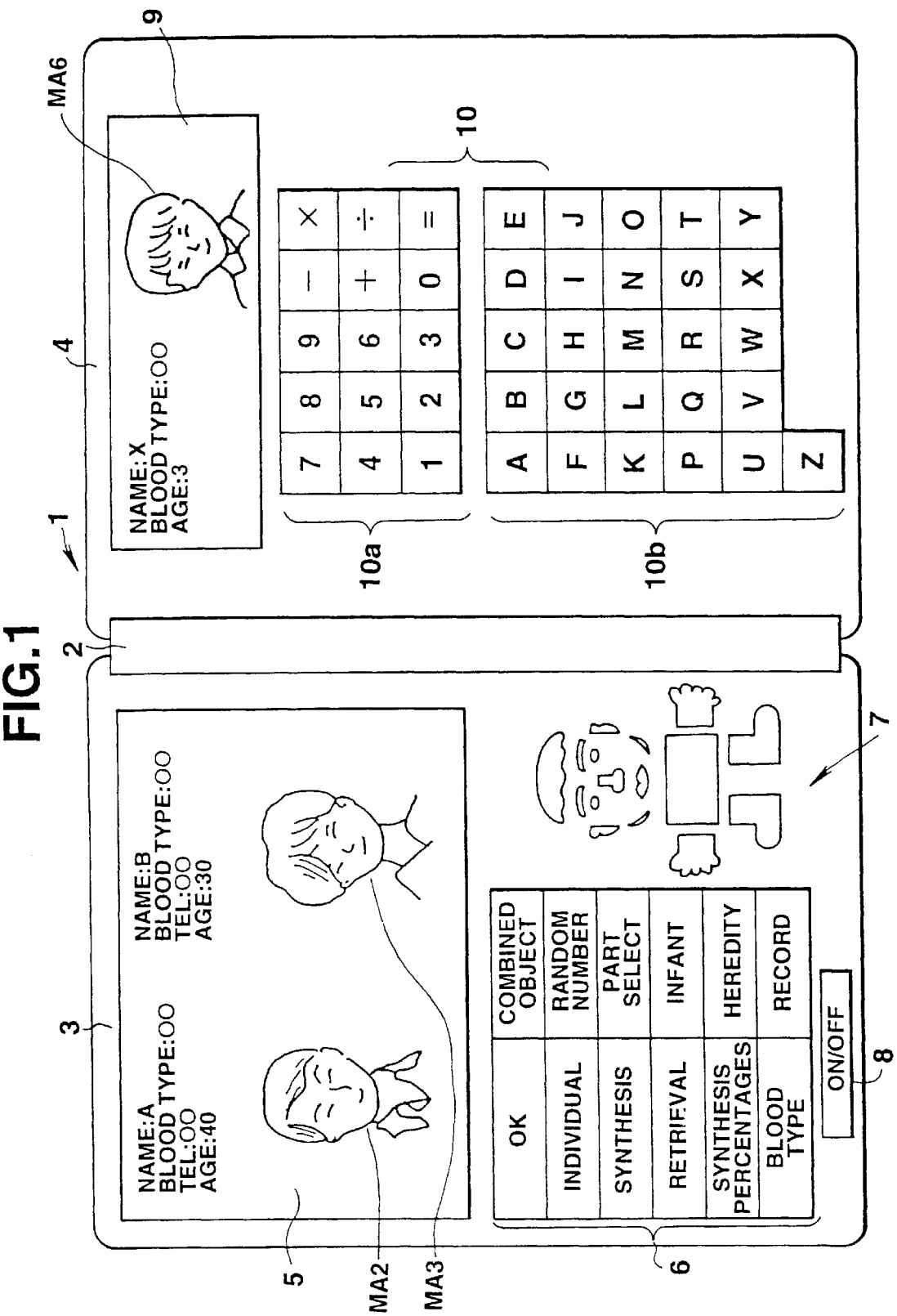
FIG. 1 is a plan view of an object image display device as a first embodiment of the present invention.

FIG. 1 shows the appearance of an object image display device as a first embodiment of the present invention. The object display device 1 of FIG. 1 is composed of front half body 3 and a rear half body 4 connected through a hinge 2. The front half body 3 is provided with a first display 5 which includes a liquid crystal display, An item switch unit 6, an ON/OFF switch 8 and a part switch unit 7 are provided below the first display 5. As shown on enlarged scale in FIG. 2, the item switch unit 6 is composed of an OK switch 6n, an individual switch 6a, a synthesis switch 6b, a retrieval switch 6c, a synthesis percentage switch 6d, a blood type 6e, a combined object switch 6f, a random number switch 6g, a part select switch 6h, an infant switch 6i, a heredity switch 6j, and a record switch 6k. The part switch unit 7 is composed of a "hair style" switch 7a, a "brows" switch 7b, an "eyes" switch 7c, and "ears" switch 7d, a "nose" switch 7e, a "contour" switch 7f, a "mouth" switch 7g, a "both arms and hands" switch 7h, a "dress" switch 7i and a "both legs" switch 7j. The rear half body 4 is provided with a second display 9 smaller in area than the first display. A data input switch 10 which includes a numerical switch 10a and an alphabetical switch 10b provided below the second display 9 in provided below the second display 9.

Two combined person-montage images MA2 and MA3 are displayed on the first display 5 while a montage image MA6 synthesized from the two montage images MA2, MA3 is displayed on the second display 9.

Figure 3:
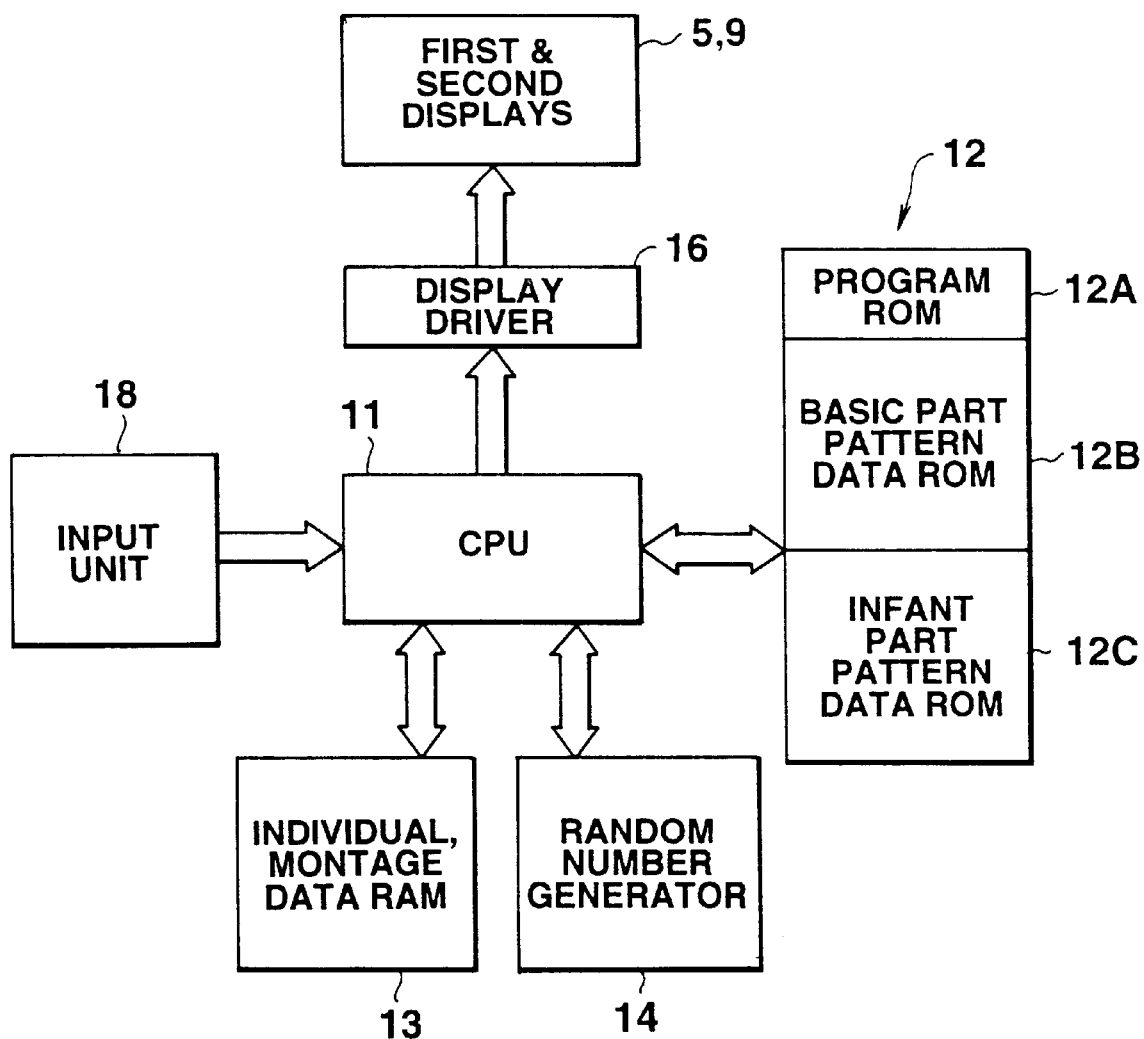
FIG. 3 is a block diagram of a whole illustrative circuit configuration of the object image display device.

FIG. 3 shows the whole circuit configuration as the object image display device 1 of this embodiment.

Switch information input to the input unit 18 composed of switches 6–10 is fed to CPU 11, which provides whole control required for the object image device 1 on the basis of the program data stored in a program ROM 12A which composes ROM 12 and random number data generated by a random number generator 14, and drives the display driver 15 which in turn drives the first and second display 5 and 9.

ROM 12 is composed of the program ROM 12A, a basic part pattern ROM 12B which stores basic part patterns, and an infant part pattern ROM 12C which stores infant part patterns. As shown in FIG. 4, the basic part pattern ROM 12B stores part patterns indicated as numbers "01"–"50" for each of 10 kinds of "contour", "hair style", "eyes", . . . , "both legs" part patterns corresponding to the switches of the part switch unit 7. As shown in FIG. 5, the infant part pattern ROM 12C stores part patterns at areas corresponding to "01"–"50" for each of 5 kinds of "contour", "hair style", "dress", "both arms and hands", "both legs" part patterns which correspond to "contour", "hair style", "dress", "both arms and hands", and "both legs" switches 7f, 7a, 7e, 7i, 7h, 7j of the part switch unit 7. The infant part pattern ROM 12C is different from the basic part pattern ROM 12B in that the former stores only 5 kinds of "contour", "hair style", "dress", "both arms and hands", and "both legs" part patterns where the features of an infant appears most remarkably. Thus, the 5 kinds of "contour", "hair style", "dress", "both arms and hands", and "both legs" part patterns are to be designated by the operation of the respective ones of "contour", "hair style", "dress", "both arms and hands", and "both legs" switch 7f, 7a, 7e, 7i, 7h and 7j of the part switch unit 7.

As shown in FIG. 6, the individual/montage data RAM 13 is composed of a display register 130, an item data area 152, a data synthesis work area 131, a montage synthesis area 132, and a reduction synthesis area 133. The item data area 152 is composed of an individual data area 134 which stores 50 individual data items at the locations "1"–"50", and a montage area 135 which stores pattern numbers of indicative parts of montage data which corresponds to the individual data items. The individual data area 134 stores the name, blood type, telephone number and age of a person input by the data input switch unit 10. The 10 kinds of "contour"— "both legs" part areas of the montage data area 135 store part patterns indicated by numbers "01"–"50" of FIG. 4 for each of the "contour", "hair style", part patterns selected by the part switch unit 7. The infant data area 136 is also composed of an individual data area 134 and a montage data area 135. The select part area 137 stores data on two combined persons and is composed of a first combined person area 138 and a second combined person area 139, which store data "0" or "1" in 10 bits indicative of each of 10 kinds of "brows", "eyes", "contour", etc. When a montage is synthesized, a part patterns is used which is stored in the combined person part area corresponding to the part area where "1" data is stored as a part pattern used for the synthesis of the montage. No part pattern is used which is stores in the part area of the combined person corresponding to a part area where "0" data is stored. In the case of the embodiment of FIG. 6, for example, "1" and "0" are stored in the first and second combined person part areas, respectively, in "contour" area. Thus, in a montage synthesis the "contour" part pattern of the first combined person is employed. For the "both legs" area, "0" and "1" are used which are stored in the first and second combined person part areas. Thus, the "both legs" part pattern of the second combined person is employed.

Therefore, when a new montage image is synthesized on the basis of the first and second combined person montage images, the part patterns stored in the combined person part area corresponding to the part area where "1" data is used mainly so that the synthesized montage image resembles the combined object montage image of data which contains more "1" than the other.

The data synthesis area 131 and montage synthesis area 132 combine the respective selected part patterns at the positions and stores the synthesized montage image. The reduced synthesis area 133 reduces and stores the created montage image for an infant image.

The operation of this embodiment will be described with reference to the flowchart of FIG. 7 and subsequent FIGURES concerned.

Figure 7:
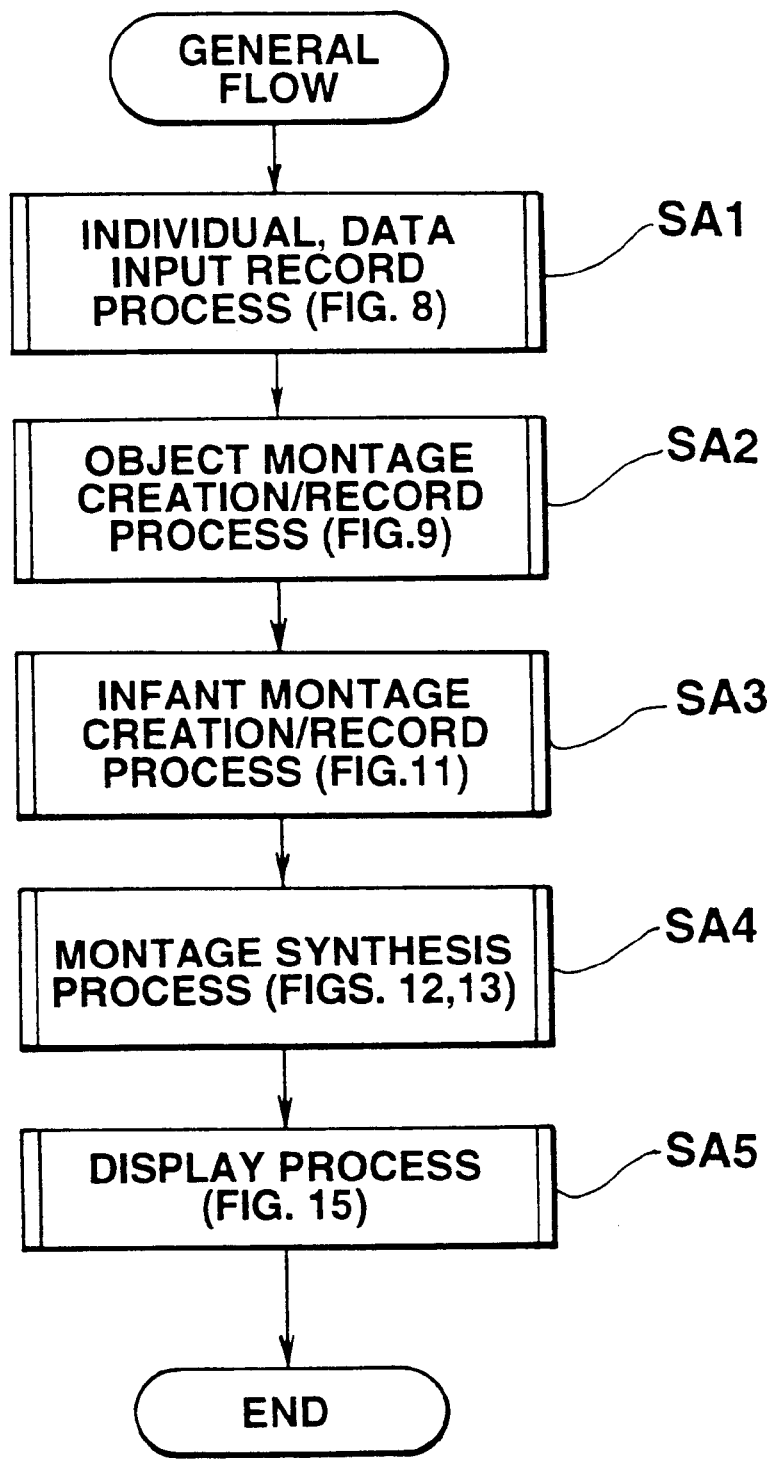
FIG. 7 is a general flow indicative of the operation of the first embodiment.
Figure 15:
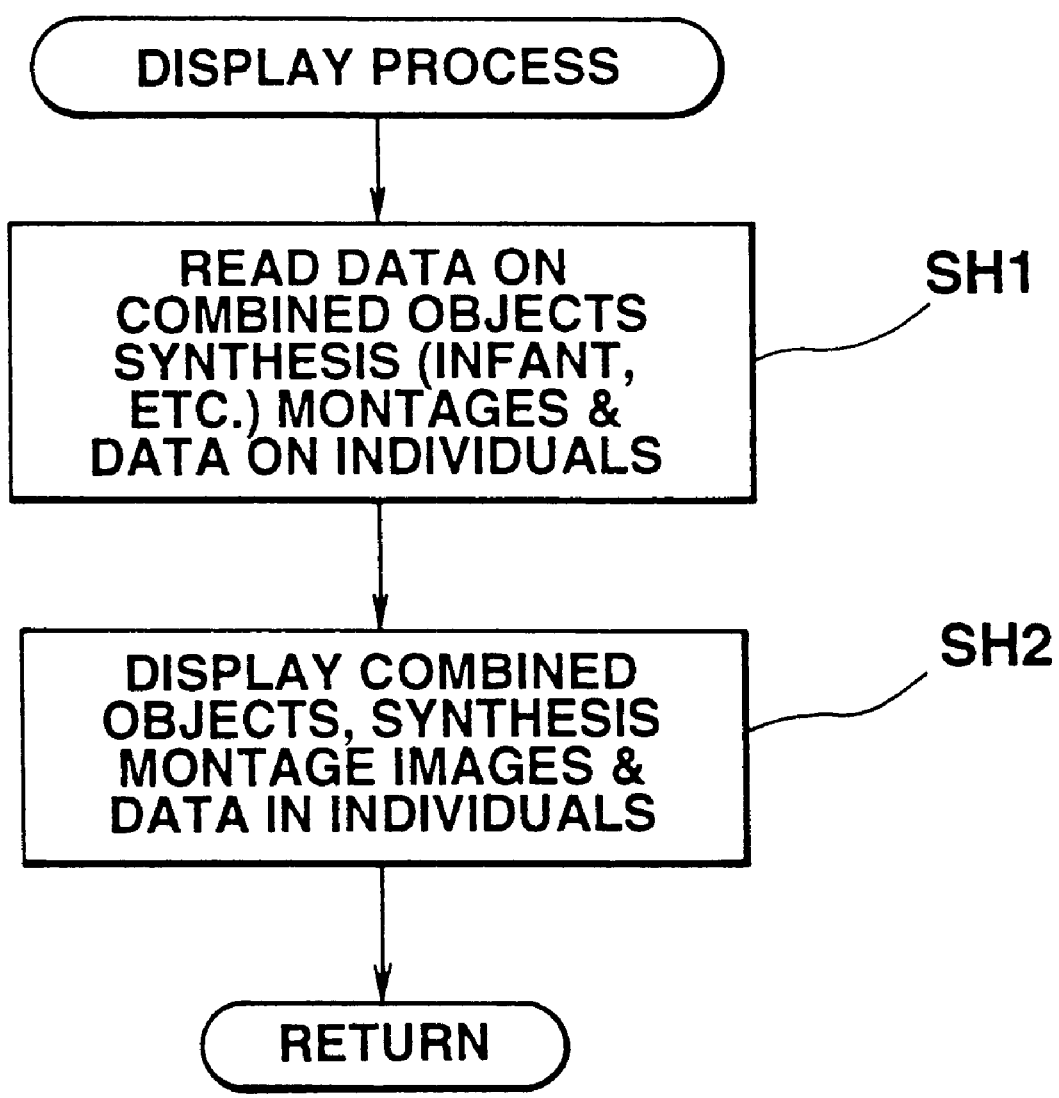
FIG. 15 is a flowchart indicative of the contents of a display process.

FIG. 7 is a general flow chart indicative of the operation of the present embodiment. (an individual data input/record process of FIG. 8 (Step SA 1) a combined person montage creation/record process of FIG. 9 (step SA2), an infant montage creation/record process of FIG. 11 (step SA3), a montage synthesis process of FIGS. 12 and 13 (step SA4) and a display process of FIG. 15 (step SA5) are performed in this order.

INDIVIDUAL DATA INPUT/RECORD PROCESS

A specified flow will be described next. First, an individual data input/record process (step SA1). is executed in accordance with the flow of FIG. 8 on condition that the individual switch 6a is operated (step SB1). If this individual switch 6a is determined to be operated, it is determined whether individual data is input by the operation of the data input switch unit 10 (step SB2). If so, this individual data is written in an individual data area 134 of the individual/montage data RAM 13 of FIG. 6 (step SB3).

Thereafter, it is determined whether the record switch 6k is operated (step SB4). If not, a looping operation involving steps SB2–SB4 is iterated until the operation of the record switch 6k is detected. Thus, during the iteration, by inputting the name, blood type, telephone number and age of the person are input by the operation of the data input switch 10, the respective input data items are written into proper ones of the items "1"–"50" of FIG. 6. Thereafter, by the operation of the record switch 6k, control returns from the flow of FIG. 8 to a general flow of FIG. 7.

COMBINED PERSON MONTAGE CREATION/RECORD PROCESS

A combined person montage creation/record process is executed at step SA2 subsequent to step SA1 of the general flow of FIG. 7. This process is executed in accordance with the flow of FIG. 9 on the condition that a combined person switch 6f is operated (step SC1). If it is determined that the switch 6f is operated, a part pattern No. "01" indicative of basic part patterns in the basic part pattern ROM 12B is set initially (step SC2). The basic part pattern No. "01" set initially set points to the respective part numbers ranging from the "contour" indicated by the part "1" of FIG. 4 to the "both legs" indicated by the part "10". Thus, part pattern numbers indicative of 10 part patterns (of a whole body) ranging from the "contour" indicated by "1" to the "both legs" indicated by "10" and stored in the column "01" at step SC2 are set initially and stored, in the montage data area 135 of the individual/montage data RAM 13.

Subsequently, a data combining process (step SC3) is executed in accordance with a flow chart of FIG. 10.

Figure 16A:
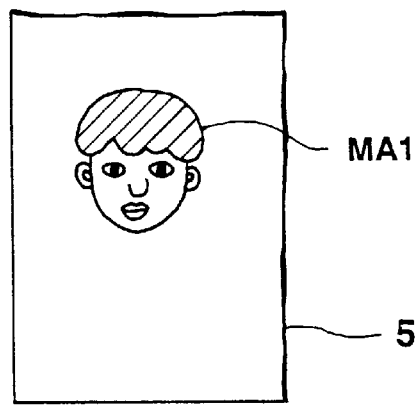
FIGS. 16A–16C each illustrative a montage image.

A "contour" part pattern No. "01" is read from among the respective part pattern numbers set initially in the montage data area 135 (step SD1). A contour part pattern corresponding to the read "contour" part pattern No. "01" is transferred to a montage synthesis area 132 of the individual/montage data RAM 13 (step SD2). The "hair style" part pattern No. "01" is read (step SD3). A hair style part pattern corresponding to the read "hair style" part pattern No. "01" is read (step SD3). A part pattern corresponding to the read "hair style" part pattern No. is transferred to the montage synthesis area 132 (step SD4). Similar processes are performed for the "eyes", "nose", "mouth", etc., are performed (step SD5). A montage image MA1 is synthesized from those transferred part patterns in the montage synthesis area 132 and displayed on the first display 5, as shown in FIG. 16A (step SA6). In FIGS. 16A–16D and 1, the respective displayed montage images MA1–MA6 are not for a whole body, but for an upper half of the whole body.

Thus, by the process at step SD6, a basic type whole-type montage image MA1 composed of a combination of respective part patterns indicated by the part pattern numbers stored in a column covering a "contour" part "01" to "both legs" part "10" of FIG. 4 is displayed as a montage image on the first display 5. If the basic type montage image MA1 is required to be corrected, the user operates the following switch operations to correct the image the basis of the image MA1, to thereby create a desired montage image on that is, at step SC4 subsequent to step SC3 of FIG. 9, it is determined whether the "contour" switch 7f of the part switch unit 7 is operated (step SC4). If so, a part pattern number corresponding to the "contour" part pattern designated by the switch 7f is changed from the initially set "01" to "02" (step SC5). This number "02" is changed and stored in the "contour" area of the individual/montage data RAM 13 and the data combining process (step SC3) is executed.

In this way, if the "contour" switch 7f is operated once, "contour" part pattern of the respective part patterns which constitute the basic type montage image MA1 displayed on the first display 5 is changed from the contour part indicated by the part pattern number "01" set initially to a contour part pattern indicated by a part pattern number "02", which then is display. In this case, since 50 kinds of "contour" part patterns are stored in ROM 12B, only the "contour" part pattern of the respective part patterns which constitute the montage image MA1 is sequentially changed by the 50 successive operations of the "contour" switch 7f, to the 50 respective "contour" part patterns, which are then displayed.

After a "contour" part pattern which is the same as, or similar to, the part pattern of the "contour" which is a part of a combined person montage image to be created is selected from the 50 kinds of "contour" part patterns and displayed on the first display 5, the operation of the "hair style" switch 7a causes the determination at step SC6 to be YES to thereby change a hair style part pattern number corresponding to the "hair style" part pattern from "01" to "02" (step SD7). Thus, the pattern of the "hair style" part of the whole body montage image is changed to a "hair style" part pattern corresponding to the part pattern No. "02", which is then displayed. Also, in this case, 50 kinds of "hair style" part patterns are stored in ROM 12B, only the "hair style" part pattern of the respective part patterns which constitute the whole body montage image can be changed by the successive operations of the "hair style" switch 7a to 50 "hair style" part patterns sequentially and the resulting images can be displayed.

Figure 2:
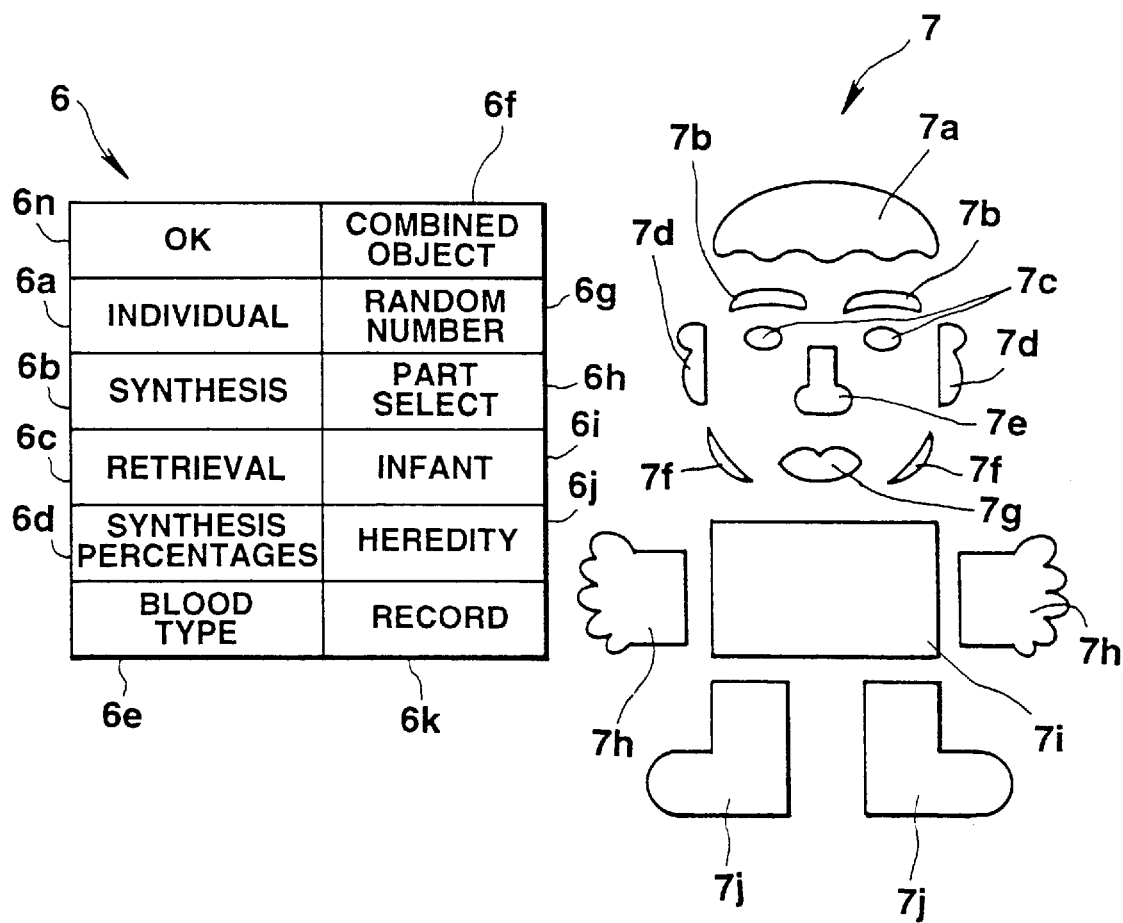
FIG. 2 is an enlarged view of the essential portion of the object image display device.
Figure 16B:
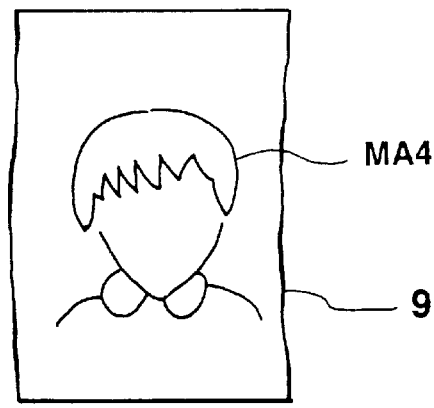
Figure 16C:
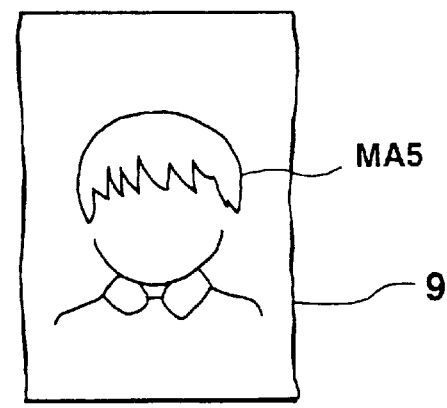
Figure 16D:
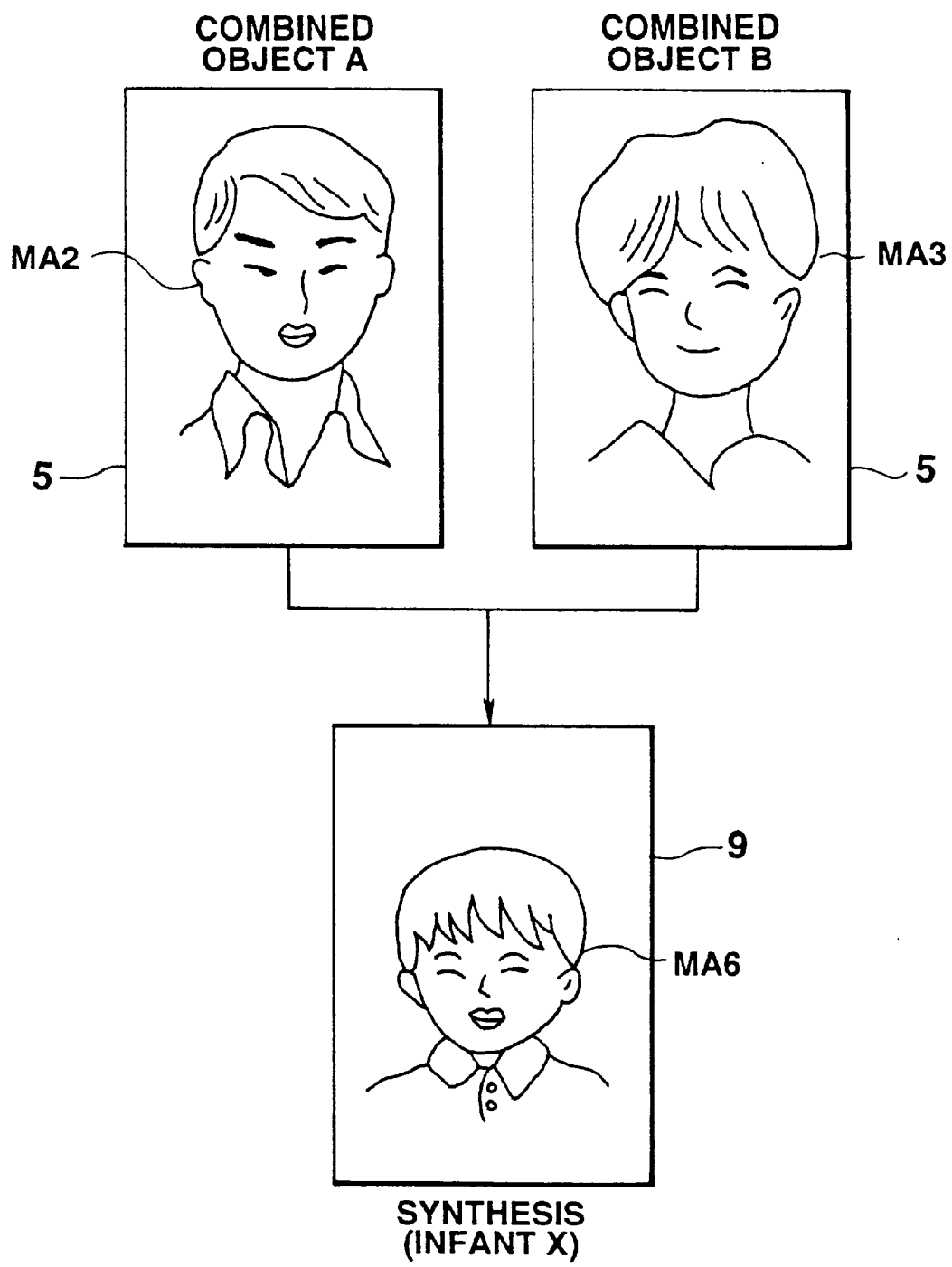
FIG. 16D illustrates combined objects and an infant's montage image synthesis from the combined objects.

Similarly, when the "eyes" switch 7c-"both legs" switch 7j of FIG. 2 are operated to change the current part pattern numbers to the part pattern numbers indicative of part patterns which are the same as or similar to, the part patterns which constitute the montage image of a combined person to be created to thereby display a whole-body montage MA2 which is the same, as or similar to, the whole body of the combined person to be created, as shown in the left-hand portion of FIG. 16D on the basis of the basic type whole-body montage image MA1 displayed initially to thereby display a whole-body montage image MA2 which 7s the same as, or similar to, the whole body of the combined person to be created.

Figure 8:
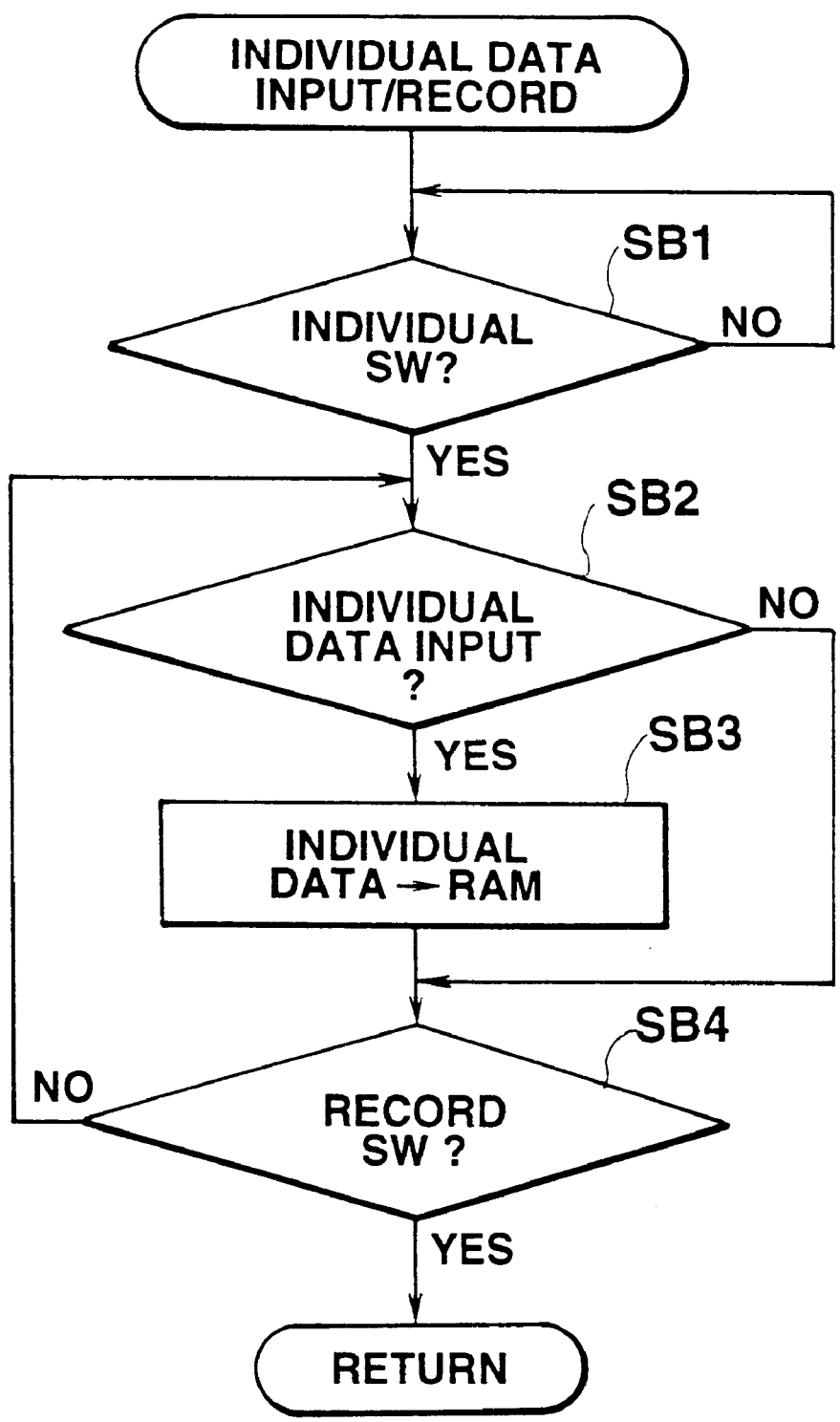
FIG. 8 is a flowchart indicative of the contents of an individual data input/record process.

If the montage image MA2 is displayed, the OK switch 6n is operated ("OK" may be input by the operation of the alphabetical switches 10b) to confirm on the display 5 the displayed state of a montage image directly before recording and then to operate the record switch 6k. This causes control to pass from step SC16 to SC17, where if the name of the combined person input as individual data in the flow of FIG. 8 is, for example, "A", the respective part pattern numbers (montage data) designated by the part switch unit 7 are recorded finally in a montage data area 135 corresponding to the item "1" and where the "A" is stored. In FIG. 6, "none" described in "both arms and hands" and "both legs" areas indicate that "OK" switch 6n and the record switch 6k have been operated without "both arms and hands" switch 7h and "both legs" switch 7j being operated. In this case, part pattern numbers are finally recorded which correspond to the patterns of all the parts except for "both arms and hands" and "both legs" part patterns.

By executing the individual data input/record process (step SA1) and the combined person montage creation/record process (steps SC1–SC17) at least twice, at least two combined person montage images MA1, MA2 are created and recorded. The present embodiment show that 50 combined object montage data items and the individual data stored in the individual data 134 are recorded in the montage data area 135 of the individual/montage date RAM 13.

INFANT MONTAGE CREATION/RECORD PROCESS

In the general flow of FIG. 7, an infant montage creation/record process is executed at step SA3 subsequent to step SA2.

Figure 11:
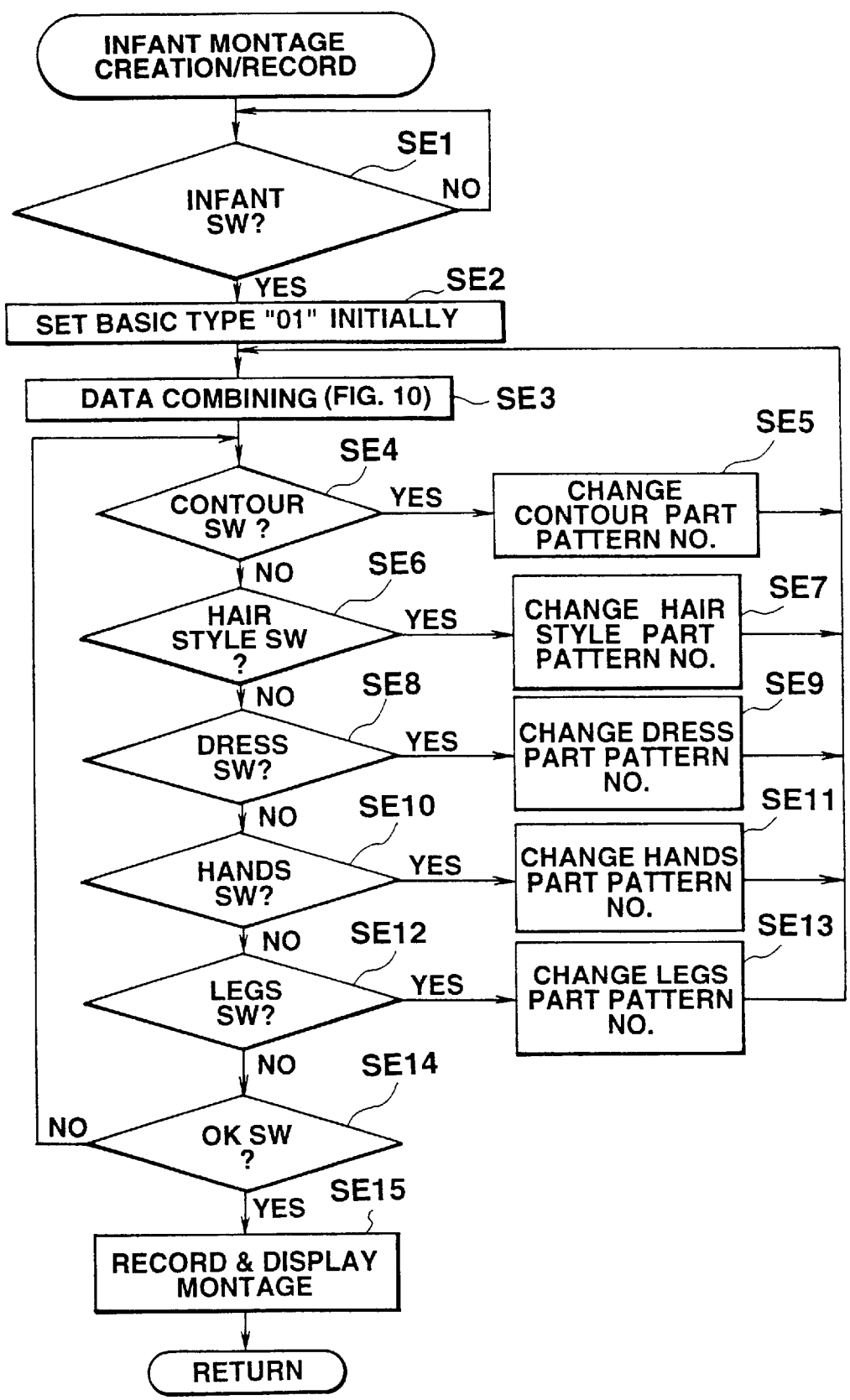
FIG. 11 is a flowchart indicative of the contents of an infant montage creation/record process.

This process is executed on condition that the infant switch 61 has been operated in accordance with the flow of FIG. 11 (step SA1). If it is determined that the infant switch 61 is operated, the process at steps SE2–SE15 is executed. The process at step SE2–SE15 is the same in contents as the flow of FIG. 9. In the present embodiment, part patterns of parts where the features of an infant are most remarkable are limited to five switches; the "contour" switch 7f which is a part switch dedicated to the infant only, a "hair style" switch 7a, a "dress" switch 7i, a "both arms and hands" switch 7h, a "both legs" switch 7j, so that the infant montage creation/record process is performed by the operation of those switches.

Figure 9:
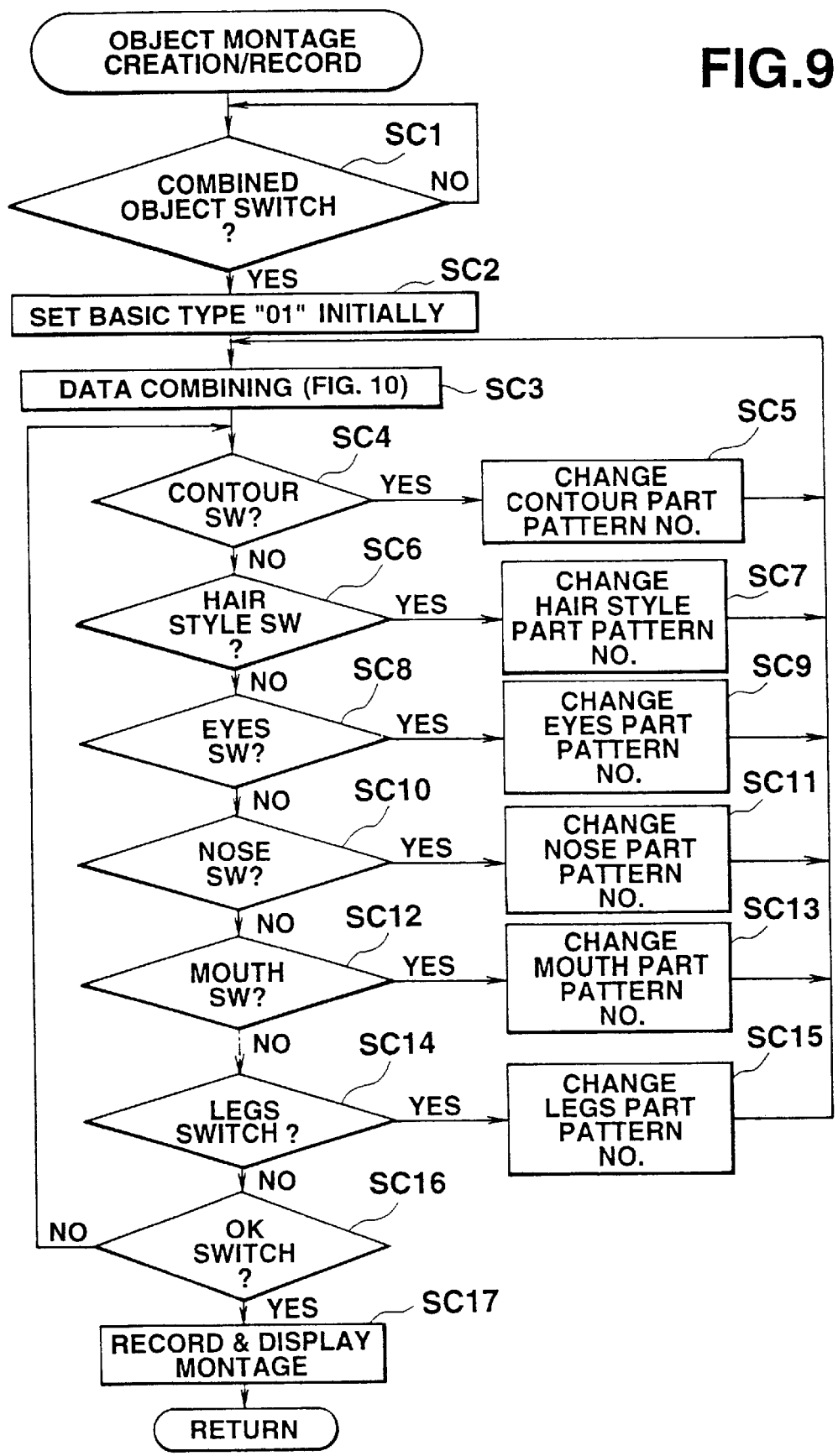
FIG. 9 is a flowchart indicative of the contents of a combined object montage creation/record process.

When the same process as combined person montage creation/record process of FIG. 9 is executed in accordance with the flow of FIG. 11, a basic montage image MA4 for a whole-body except for "eyes", "nose", "mouth", "brows", and "ears" is displayed initially as shown in FIG. 16B (step SA2). Thus, a corrected montage image MA5 composed of a combination of a "contour", "hair style", "dress", "both arms and hands", "both legs" part patterns designated by the operation of the "contour" switch 7f, "hair style" switch 7i, "both arms and hands" switch 7h, and "both legs" switch 7j on the basis of the montage image MA4 is displayed as shown in FIG. 16C. When the "OK" and "record" keys 6n and 6k are operated, the part pattern numbers indicative of the respective part patterns which constitute the corrected montage image MA5 are recorded finally in the infant data area 136 of FIG. 6.

MONTAGE SYNTHESIS PROCESS

In the general flow of FIG. 7, a montage synthesis process is executed at step SA 4 subsequent to step SA3. This process involves partly combining a plurality of combined person montage images to create a new synthesized montage image.

Figure 12:
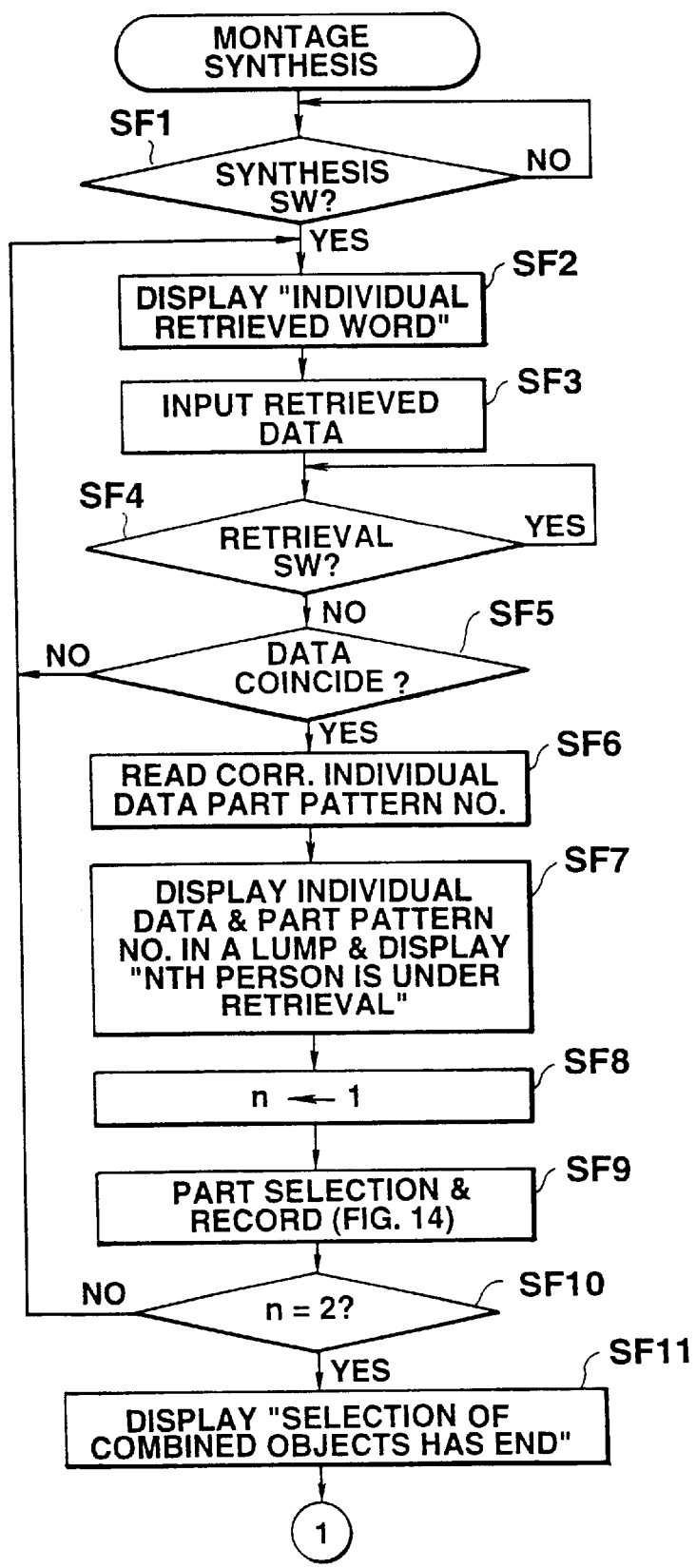
FIG. 12 is a flowchart indicative of the contents of a montage synthesis process.
Figure 13:
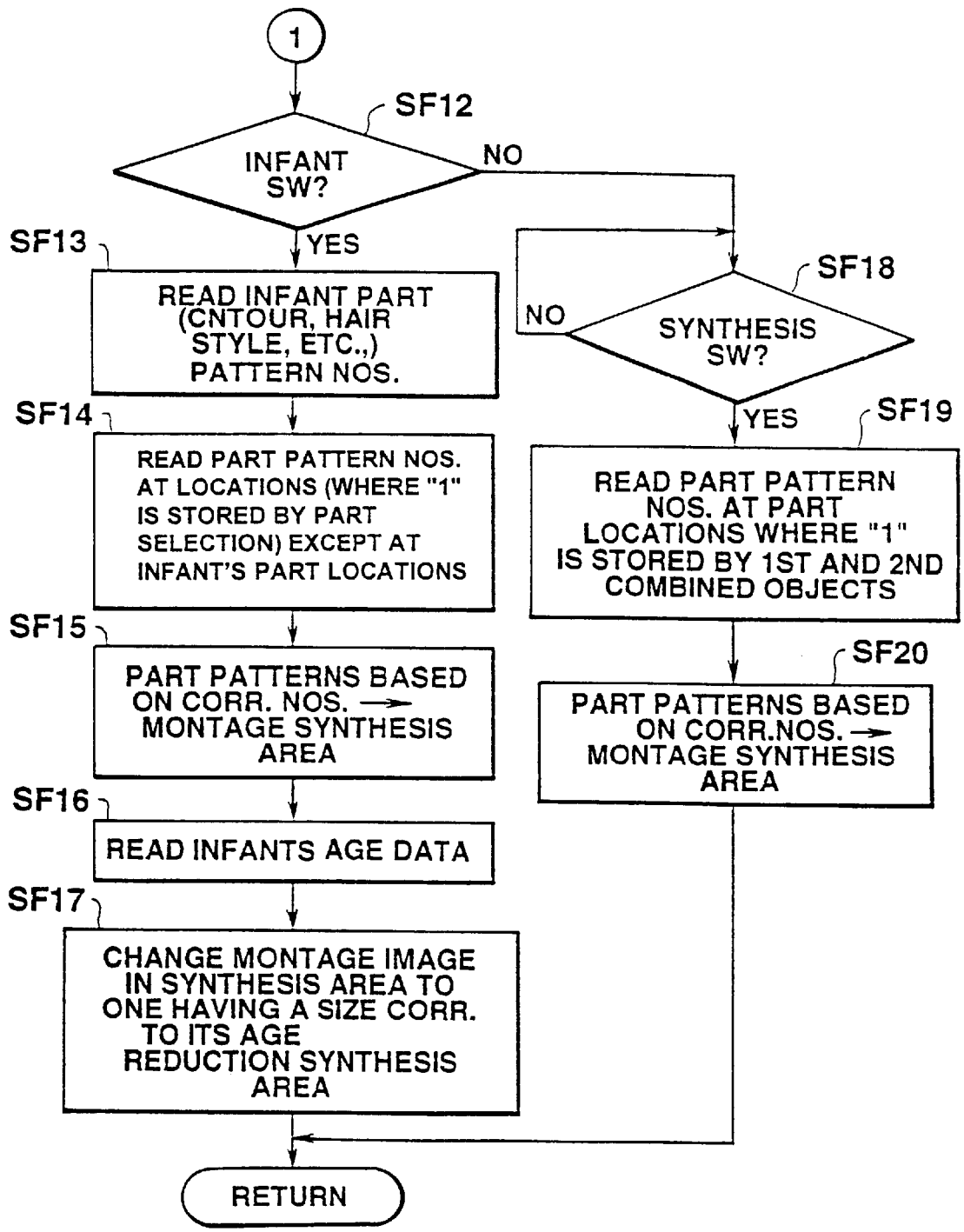
FIG. 13 is a flowchart indicative of the contents of a montage synthesis process subsequent to FIG. 12.

This process is executed on condition that the synthesis switch 6b is operated in accordance with a series of flows of FIGS. 12 and 13 (step SF1). When the operation of the synthesis switch 6b is determined, "after individual retrieval ?" is displayed on the first display 5 (step SF2).

The user operates the data input switch 10 to input as retrieval data the same name as any one of the names "A", "B", "C", . . . on individual data stored beforehand in the individual montage RAM 13 in accordance with that display (step SF3). It is then determined whether the retrieval switch 6c is operated (step SF4). If so, it is determined whether the name which is the retrieval data input at step SF3 coincides with any one of the names as the individual data (step SF5).

When both data items coincide and a retrieved name input by the operation of the data input switch 10 is stored in the individual data area 134 of the individual/montage data RAM 13, the individual data involving that coincidence and the respective part pattern numbers corresponding to the individual data are read (step SF6). The read individual data and the respective part pattern numbers and the characters "as nth person is being retrieved" are displayed together (step SF7). Thus, when the data input switch unit 10 is operated to input, for example, "A"'s name, "A"'s input name, blood type, telephone number and age as well as part pattern numbers "01", "02", "02", . . . corresponding to the respective part patterns which constitute "A"'s montage image MA2 are displayed together on the displays and a "first person is being retrieved" is also displayed on the first display 5.

PART SELECTION/RECORD PROCESS

An internal counter n (not shown) of CPU 11 is counted up (SF8) and part selection/record process is executed (SF9). This process includes a process for determining a selected one of the part patterns of the two combined person montage images as each of the part patterns of a synthesized montage image to be created and a process for recording a part pattern number corresponding to the selected part pattern.

Figure 14:
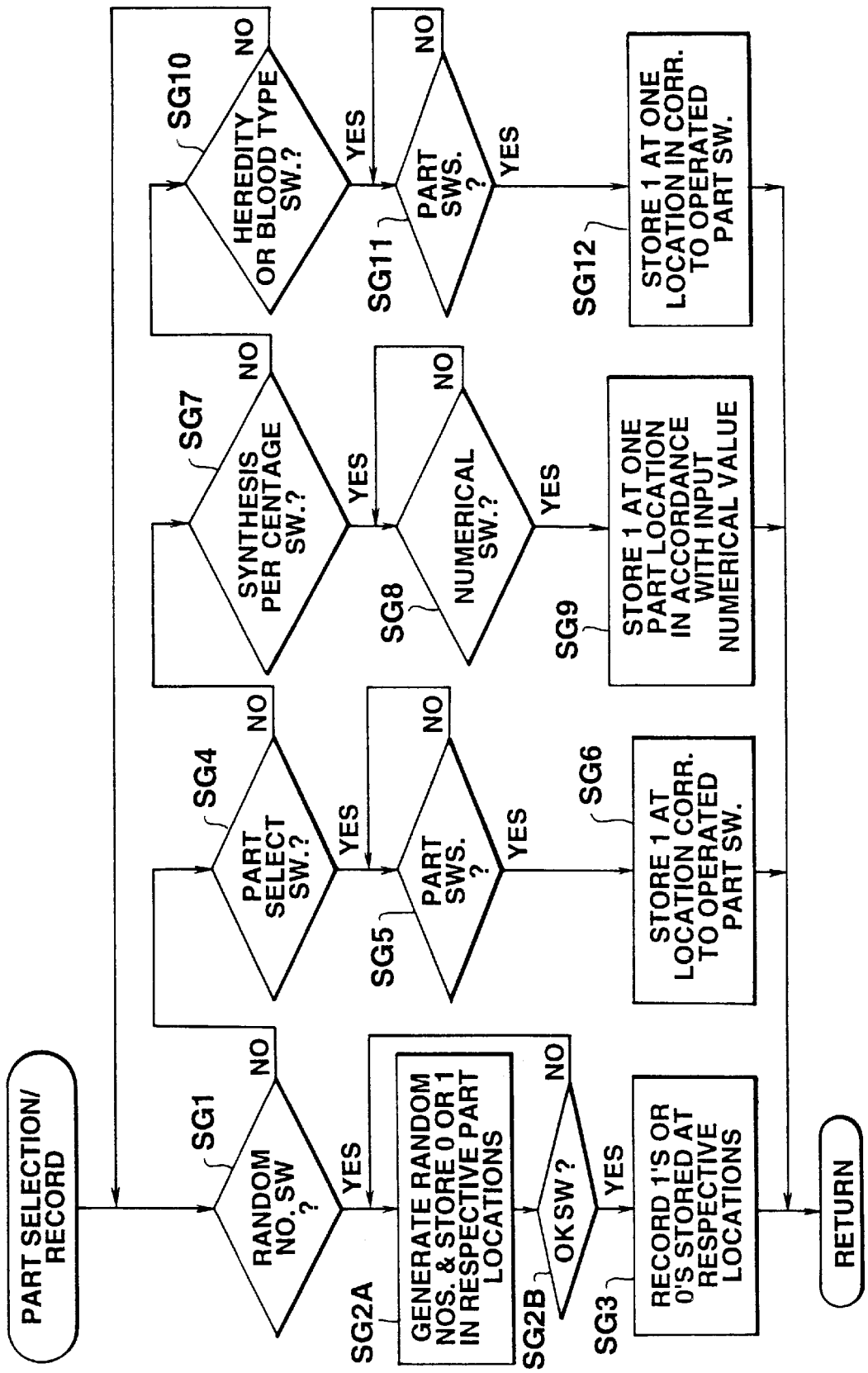
FIG. 14 is a flowchart indicative of the contents of the part selection/record process.

This process is executed on condition that any one of the random number switches 6g, the part select switch 6h, a synthesis percentage switch 6d, the heredity 6i and the blood type switch 6e has been operated at steps SG1, SG4, SG7, and SG10 in accordance with the flow of FIG. 14.

First, if it is determined that the random number switch 6g has been operated (YES at step SG1), the random number generator 14 is operated to generate random number date "1" or "0" sequentially and random by (step SG2). The "1" or "0" generated sequentially and randomly from the random number generator 14 are rewritten at 10 "contour", "hair style", . . . , part locations in the first and second combined person areas 138 and 139 (step SG2A). The random number data stored beforehand at the part locations is rewritten with random data generated sequentially and randomly later. When the user operates the OK switch 6n an time after the random data is generated randomly and sequentially (step SG2B), the random number data "1" or "0" rewritten in the part areas are finally recorded (step SG3). In this case, when "1" is stored at one of the respective part locations of the first and second combined person areas 138 and 139, "0" is automatically recorded in the other corresponding part area in order to prevent double use of the part patterns of the combined persons corresponding to each other. Thus, "1" is automatically recorded in any one of the respective part locations of the first and second combined person areas 138 and 139 irrespective of the user's intention. In the present embodiment, since "1" is recorded at any one of the part locations of the first and second combined person areas 138 and 139 depending on the random number data generated randomly and sequentially by the random number generator 14, "1's" can be recorded at all the part locations in an extreme case. Alternatively, "1" or "0" generated randomly and sequentially from the random number generator 14 may be stored sequentially at the 10 respective part locations of the first and second combined person areas 138, 139 until random number data is stored at all the part locations, at which time the "1" or "0" of the random number data stored at the respective part locations may be are recorded finally. Alternatively, "1" or "0" generated randomly and sequentially from the random number generator 14 may be rewritten repeatedly at the 10 respective part locations of the first and second combined person areas 138, 139 until a predetermined interval of time has elapsed, at which time random number data "1's" or "0's" stored at the part locations may be recorded finally.

When it is determined that the part select switch 6h is operated without the random number switch 6g being operated (YES at step SG4), it is determined at the next step whether any one of the switches 7a–7j of the part switch unit 7 has been operated (step SG5). If so, "1" is stored at that part location of the first combined person area 138 corresponding to the part designated by the operated one of the part switches 7a–7i (step SG6). Therefore, for example, when the "contour" switch 7f is operated, "1" is stored at the "contour" area of the first combined-person area 138. When the "hair style" switch 7a is operated, "1" is stored at the "hair style" area. Once "1" is stored at a area in the first combined person area 138, "0" is automatically stored at the part location corresponding to "contour" part areas, etc., of the second combined person area 139.

When it is determined that the synthesis percentage switch 6d has been operated without the part select switch 6h being operated (YES at step SG7), it is determined at the next step whether the numerical switch 10a has been operated (SG8). If so, "1" is stored only at one of the part locations of the first and second combined-person areas 138 and 139 (step SG9). For example, when a numerical value "50" is input by the operation of the numerical switch 10a to set the synthesis percentage of the first and second combined persons at 50 percent, "1's" which are the same in number (in the case of present embodiment, 5) are stored at the respective part locations of the first and second combined person areas 138 and 139. When numerical values "80" and "20" are input by the operation of the numerical switch 10a in order that the synthesis percentages are "80%" and "20%", respectively, "1's" the number of which corresponds to "80" and "1's" the number of which corresponds to "20" are stored at the respective part locations of the first and second combined person area 138 and 139. In the case of this embodiment, since the number of part locations areas is 10, 8 "1's" and 2 "1's" are stored at the part locations in the first and second combined person areas 138 and 139, respectively. Also, in this case, if "1" is stored at one of the part locations of the first and second combined person areas 138 and 139, "0" is automatically stored at the corresponding other part area locations of the combined person areas 138 and 139.

When it is determined that the heredity switch 6j or blood type switch 6e has been operated, it is determined at the next step whether the part switch unit 7 is operated (step SG11). If so, "1" is stored in only at one of the part locations of the first and second combined person areas 138 and 139 and corresponding to each other (step SG12). That is, when the heredity switch 6j or blood 6e is operated and the part switch unit 7 is then operated, "1" or "0" is stored at a part location corresponding to the part designated by the operation of the part switch unit 7 in accordance with probability data depending on the king of "blood type" which constitutes the individual data area 134 of the combined person, or probability data obeying on a of heredity and conforming to the kind of the "blood type" and the "age" which constitutes the individual data area 134. Since those probability data items are stored beforehand in ROM 12, "1" or "0" is stored depending on the probability data items.

At step SF10 subsequent to step SF9 of FIG. 12 it is determined whether the count of counter is n=2. If not, the process and determination starting at step SF2 are performed again. Thus, the part selection/record process of FIG. 14 is performed again for a newly selected second combined person.

When it is determined that n=2 at step SF10, the part selection/record process is completed for the two combined persons. Thus, "Selection of the combined persons has been completed" is displayed on the first display 5 (step SF11).

Control then passes to step SF12 of FIG. 13, where it is determined whether the infant switch 6*i* is operated to determined whether an infant montage image is to be created as a synthesized montage image. If so, particular infant part pattern numbers are read which are indicative of "contour", "hair style", "dress", "both arms and hands", and "both legs" only stored in the infant data area 136. After this process has been completed, part pattern numbers in other part locations (for the "eyes", "nose", "mouth", "brows", and "ears") other than the above infant part locations which constitute the infant data area 136 and where "1's" are stored by the part selection of step SE9 (FIG. 12) are read (step SF14). In the case FIG. 6 embodiment, "50", "01", "01", "40" and "30" are stored only at the "contour", "hair style", "dress", "both arms and hands", "both legs" part locations of the infant data 136, and no part pattern numbers are stored at other part locations (indicated by "none").

Since at this time the first and second combined persons are already determined and "1's" or "0's" are stored at the respective part areas of the first and second combined person areas 138 and 139, combined person part pattern numbers are then read which correspond to other "eyes", "nose", "mouth", "brows", "ears" part locations of the infant data area except for the "contour", "hair style", and "dress" part locations and where "1's" in the first and second combined person areas 138 and 139 are stored. In the case of the FIG. 6 embodiment, since "1's" are stored in the "contour", "hair style", "mouth", "dress" and "both arms and hands" part locations which constitute a portion of the first combined person area 138 and the "eyes", "nose", "brows", "ears", and both legs part locations which constitute a portion of the second combined person area 139, the part pattern numbers stored in the part locations of the combined person areas 138 and 139 where "1's" are stored can be read. However, the part pattern numbers stored in the "contour", the "hair style", "dress", both arms-and hands and legs part locations are not read, but the part pattern numbers stored in the "contour", "hair style", "dress", both arms-and hands and legs part locations of the infant data area instead are read preferentially.

As a result, in the case of the present embodiment, the part pattern numbers encircled in FIG. 6 are read as follows:

The first combined person "A"; "30" (mouth):

The second combined person "B"; "50" (eyes), "20" (nose), "03" (brows), "04" (ears): and The infant "X"; "50" (contour), "01" (hair style), "01" (dress), "40" (both arms and hands), and "30" (both legs).

Thereafter, part patterns corresponding to the read part pattern numbers are read from the basic part pattern ROM 12B and infant part pattern ROM 12C and transferred to the montage synthesis are 132, where a montage is synthesized from those part patterns (step SF15).

Subsequently, infant's "age" data is then read from the "age" location in the individual area 134 of RAM 13 (step SF16). The montage image is reduced in size to a one corresponding to the read infant's age, and data on the obtained image is stored in the reduced size synthesis areas 133 of RAM 13 (step SF17). In this case, data on the rate of reduction of the montage image corresponding to the infant's age is stored as conversion table in ROM 12.

As a result, since the reduced infant's montage image is composed of a combination of the "mouth" part pattern of the first combined person "A" and the "eyes", "brows", and "ears" part patterns of the second combined person "B" except for the "contour", "hair style", "dress", "both arms and hands", and "both legs" of the infant "X". The resulting montage in this case more resembles the montage of the second combined person "B" than that of the first combined person "A".

When at step SF12 it is determined that the infant switch 6*i* is not operated, control passes from step SF12 to step SF18, where it is further determined whether the synthesis switch 6*b* has been operated. If so, the part pattern numbers at the part locations where "1's" is stored by part selection of step SF9 (FIG. 12) among the part locations of the first and second combined person areas 138 and 139 are read since only the part patterns of the combined persons "A" and "B" are to be used without using the part patterns of the infant "X" for the resulting montage image (step SF19).

As a result, in the case of this embodiment, the following part pattern numbers hatched in FIG. 6 are read;

The first combined person "A": "01" (contour), "02" (hair style), "30" (mouth), and "03" (dress);

The second combined person "B": "50" (eyes), "20" (nose), "03" (brows), "04" (ears), "03" (dress).

In this case, since no part pattern numbers are stored at the "both arms and hands" and "both legs" part locations, then data are not read.

Part patterns corresponding to the read part pattern numbers are read from the basic part pattern ROM 12B, transferred to the montage synthesis area 132, where a montage is synthesized from those part patterns and stored (step SF20).

Display process

In the general flow of FIG. 7, a display process is executed at step SA5 subsequent to step SA4. This process is performed in accordance with the flow of FIG. 15. That is, the individual's data and montage data of the combined persons "A" and "B" stored in the individual data area 134 and montage data area 135 in RAM 13, and the individual data stored in the individual data area 134 for an infant "X" to be synthesized are read (step SH1). Thereafter, as illustrated in FIG. 1, the respective individual data items of the read combined persons "A" and "B" are displayed on the first display 5, and the "A" and "B" montage images MA2 and MA3 on the basis of the read combined persons "A" and "B" montage data are displayed below those individual data items. The read infant "X's" individual data is displayed on the second display 9, and a montage image MA6 corresponding to the infant "X's" montage image stored in the montage synthesis area 132 or the reduction synthesis area 133 in the montage synthesis process (FIGS. 12 and 13) at step SA4 is displayed below the displayed "X's" individual data on the basis of the "X's" montage image (step SH2).

As described above, as illustrated in FIGS. 1 and 16D, an infant's montage image MA6 having the features of one combined person "A"'s "mouth" and the features of the other combined person "B"'s "eyes", "nose", "brows", and "ears" is rapidly and easily created and displayed by a simple switching operation. A synthesized montage image having some of the features of one combined person's montage image and some of the features of the other combined person's montage image is created and displayed rapidly and easily by a simple operation. Thus, for example, by creation of a lover or husband's and wife's montage images, an infant or synthesis montage image additionally having same or all of the features of the lover or husband's and wife's montage images is created rapidly and easily.

When (1) random number data is generated randomly by the operation of the random number switch and recorded at part locations in one of the first and second combined person areas 138 and 139 steps SG 1–SG 3, (2) the respective part patterns which constitute the first and second combined person montage images are used randomly to create a synthesized montage image composed of the randomly combined part pattern is created, the montage image can be an unexpected one easily irrespective of the user's intention.

If the combination percentages of the first and second combined person montage images are designated by the operation of the synthesis percentage switch 6d and the numerical switch 10a are designated, a synthesized montage image is created depending on the combination percentages. Thus, for example, a synthesized montage image which more resembles one of the combined person montage images is created.

By the operation of the heredity switch 6j and the blood type switch 6e, a synthesized montage image is created depending on the heredity or blood type element.

In the case of the embodiment of FIG. 16D, the infant switch 6i is operated. Thus, the respective montage image MA2, MA3 of the combined persons "A", "B" as well as the montage image MA6 of the infant "X" are displayed. If the infant switch 6i is not operated but the synthesis switch 6b is operated, the respective montage images MA2, MS3 of the combined persons "A" and "B" are displayed on the first display 5 while a synthesized montage image MA6 created newly on the basis of those montage images MA2, MA3 is displayed on the second display 9.

While in the present embodiment when it is determined at step SF11 of FIG. 12 that n=2, selection of combined person is terminated and the number of combined persons is limited to 2, three or more combined persons may be selected.

While the combined objects are human being and the resulting synthesis is also a human being, the present invention is not limited to that particular example. For example, the combined objects are human being's image and animal's image, and the synthesis may be a combination of a human image and animal's image.

While in the present embodiment the synthesis of an infant's face montage image or a whole-body montage image obtained by a combination corresponding ones of the respective parts of two combined adult images and an infant's image has been illustratively displayed, a synthesized montage image may be created and displays as a combination of corresponding ones of the respective part patterns of two adult images, two children's images, or an adult and a child image.

While in the present embodiment a single infant montage image synthesized from two combined object images has been illustrated as being displayed, on the display the synthesized montage image may be printed out without or in addition to such display of the synthesized image.

SECOND EMBODIMENT

FIG. 17 shows the appearance of an object image display device as a second embodiment of the present invention. In the second embodiment, the same reference numeral is used to denote the same element of the second and first embodiments and further description of that element will be omitted.

An item switch unit 6, an ON/OFF switch unit 8, and a part switch unit 7 are provided below a first display 5 provided on a front unit 3 of the object image display device 1.

The item switch unit 6 is provided with an individual switch 6a, an OK switch 6n, a retrieval switch 6c and a record switch 6k which are similar to those of the first embodiment, a montage creation switch 26a, a weight change designation switch 26d, an intake calory change designating switch 26e and a comparison switch 26f. As in the first embodiment, the part switch unit 7 is composed of a hair style switch 7a, a brows switch 7b, an eyes 7c, an ears 7d, a nose switch 7e, a contour 7f, a mouth switch 7g, a both-arms-and-hands switch 7h, a dress switch 7i, and an both-legs switch 7j. A first display 5 having a larger display area is used to display a montage image and related characters while a second display 9 having a smaller area is used to display a command to operate a data input switch 10 and others such as the result of calculations.

Figure 18:
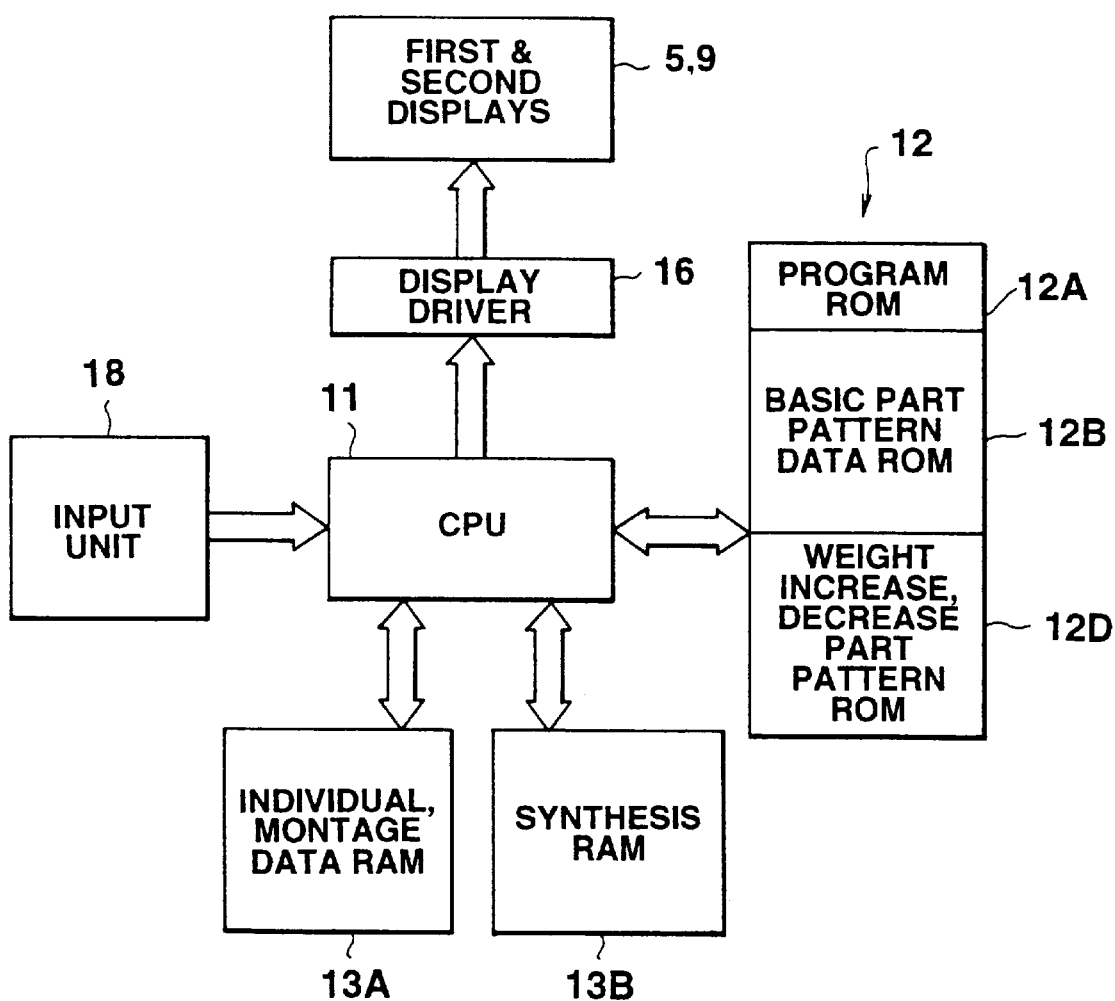
FIG. 18 is a block diagram of a whole illustrative circuit configuration of the object image display device.

FIG. 18 is a block diagram of the whole structure of the object image display device 1 as the second embodiment.

In the second embodiment, ROM 12 connected to CPU 11 is provided with a program ROM 12A, a basic part pattern ROM 12B, and a weight increase/decrease part pattern ROM 12D. The basis part pattern ROM 12B is similar to the basic part pattern ROM 12B of FIG. 19 and, in this embodiment, stores 50 part patterns of each of "contour", "hair style", "eyes", "month" . . . , "both legs" which correspond to the respective part switches 7a–7j of the part switch unit 7 are stored in correspondence to pattern numbers "1"–"50".

As shown in FIG. 20, the weight increase/decrease part pattern ROM 12D stores 9 kinds of "contour" part patterns corresponding to weight change "+20 Kg", "+5 Kg", . . . , "0 Kg", . . . , "−20 Kg" which are different at intervals of 5 Kg in this order in each of columns indicated by the part pattern numbers "01"–"50" corresponding to 50 "contour" part patterns stored in the basic part pattern ROM 12B of FIG. 19. In this case, 50 "contour" part patterns stored in a "0 Kg" row of the weight increase/decrease part patterns are identical to the 50 "contour" part patterns indicated by pattern numbers "01"–"50" in the basic part pattern ROM 12B of FIG. 19. ROM 12D stores "contour" part patterns having shapes corresponding to weights which are sequentially reduced to "−20 Kg" at intervals of "5 Kg" and "contour" part patterns having shapes corresponding to weights sequentially increased to "+20 Kg" at intervals of "5 Kg" below and above the "contour" part pattern in the "0 Kg" row at the part locations corresponding to the part pattern numbers "01"–"50". Thus, the weight increase/decrease part pattern ROM 12D stores 450 (50 "contour" part patterns×9 (the number of weight increases/decreases)). The respective part pattern Nos. after the weight is increased/decreased are written as follows: For example, the part pattern number is "01" and an increase in the weight is "+5 Kg" compared to the current weight value, the resulting part pattern number is written as "01+5" while when the part pattern is "01" and a decrease in the weight is "−20 Kg", it is described as "01–20". That is, the leading numeral in the bracket expresses a basic part pattern number which can be "01"–"50" and the trailing numeral expresses an increase/decrease in the weight "−20", "0", "+20".

As shown in FIG. 21, the individual/montage data RAM 13A is provided with a display register 130, an item data area 152, a designated weight change value area 153, a designated intake calory change value area 154, a montage data area 155 for the designated weight change value, and a montage data area 156 for calory change. The item data area 152 is composed of an individual data area 134 and a montage data area 135. The individual data area 134 stores the name, address, weight, weight measurement date, height, height measurement date, and other predetermined matters for each item No. The montage data area 135 stores the respective part pattern numbers indicative of the montage data input by the operation of the part switches 7a–7j at the corresponding part locations. The designated weight value area 153 stores the designated current weight change value ± of increases/decreases input by the user's operation of the data input switch 10 for the respective objects "1"–"50" in the item data area 152 under the operation of the weight designation switch 26d. The designated intake calory change value area 154 stores the designated intake calory change values input by the operation of the data input switch 10 for the respective objects "1"–"50" at locations of the item data area 152 under the operation of the designated intake calory switch 26e.

The montage data area 155 for weight change stores part pattern numbers each corresponding to a "contour" part pattern having a shape depending on a designated weight change value by which the current weight value of a particular one of the objects for "1"–"50" in the item area is increased/decreased to a designated weight value. For example, when the current weight value is increased greatly to a designated one, the montage data area 155 stores a part pattern number indicative of a "contour" part pattern having a fat shape corresponding to the increased designated weight change value.

The montage data area 156 for calory change stores part pattern numbers each indicative of a "contour" part pattern having a shape depending on a designated intake calory change value by which the current intake calory value of a particular one of the objects for the items "1"–"50" is increased/decreased. For example, when the current intake calory value is increased greatly to a designated one, the montage data area 155 stores a part pattern number indicative of a "contour" part pattern having a fat shape corresponding to the increased designated intake calory change value.

The operation of the second embodiment will be described with reference to the flowchart of FIG. 22 and subsequent FIGURES concerned.

Figure 22:
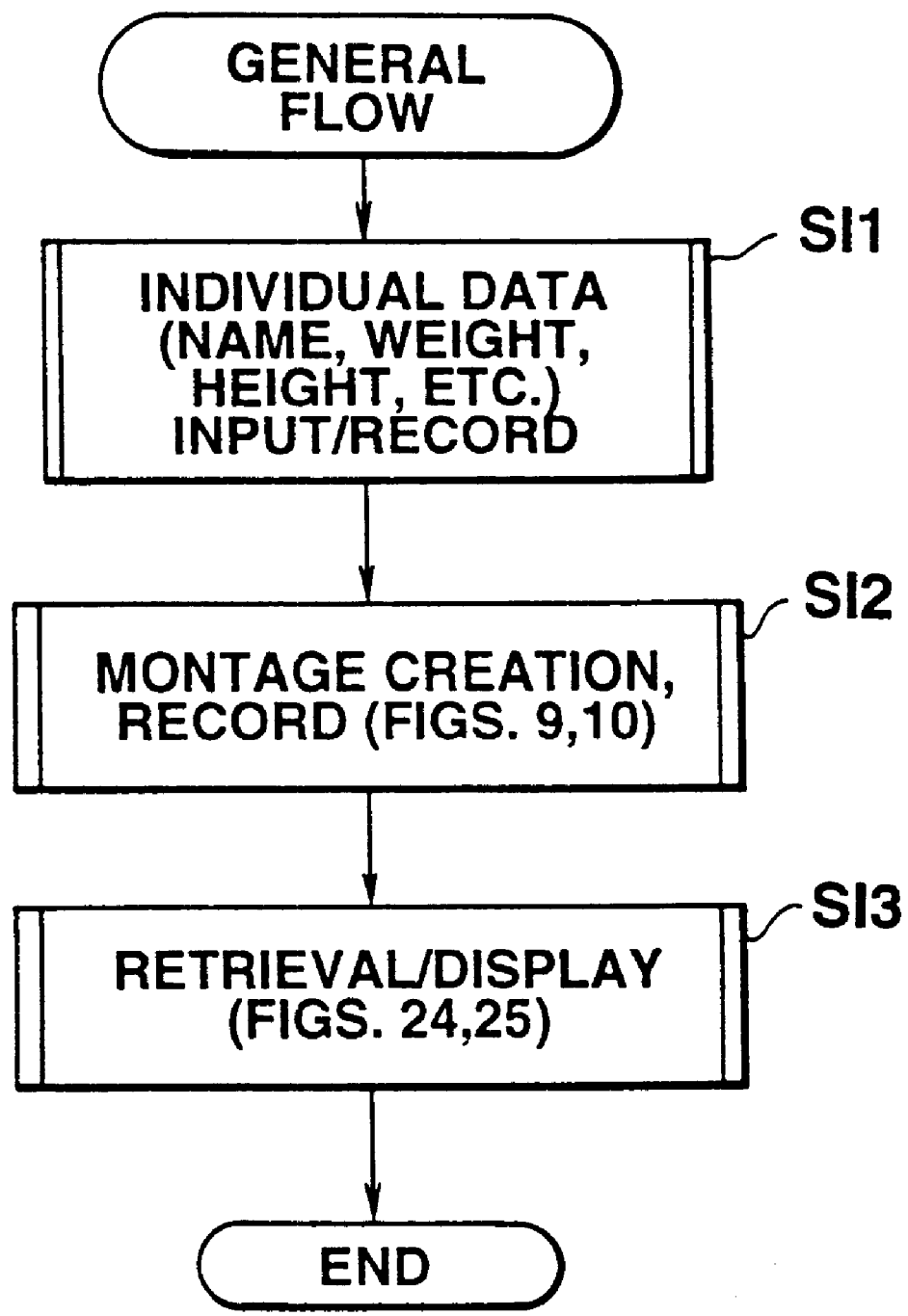
FIG. 22 is a general flow indicative of the operation of the second embodiment.
Figure 23:
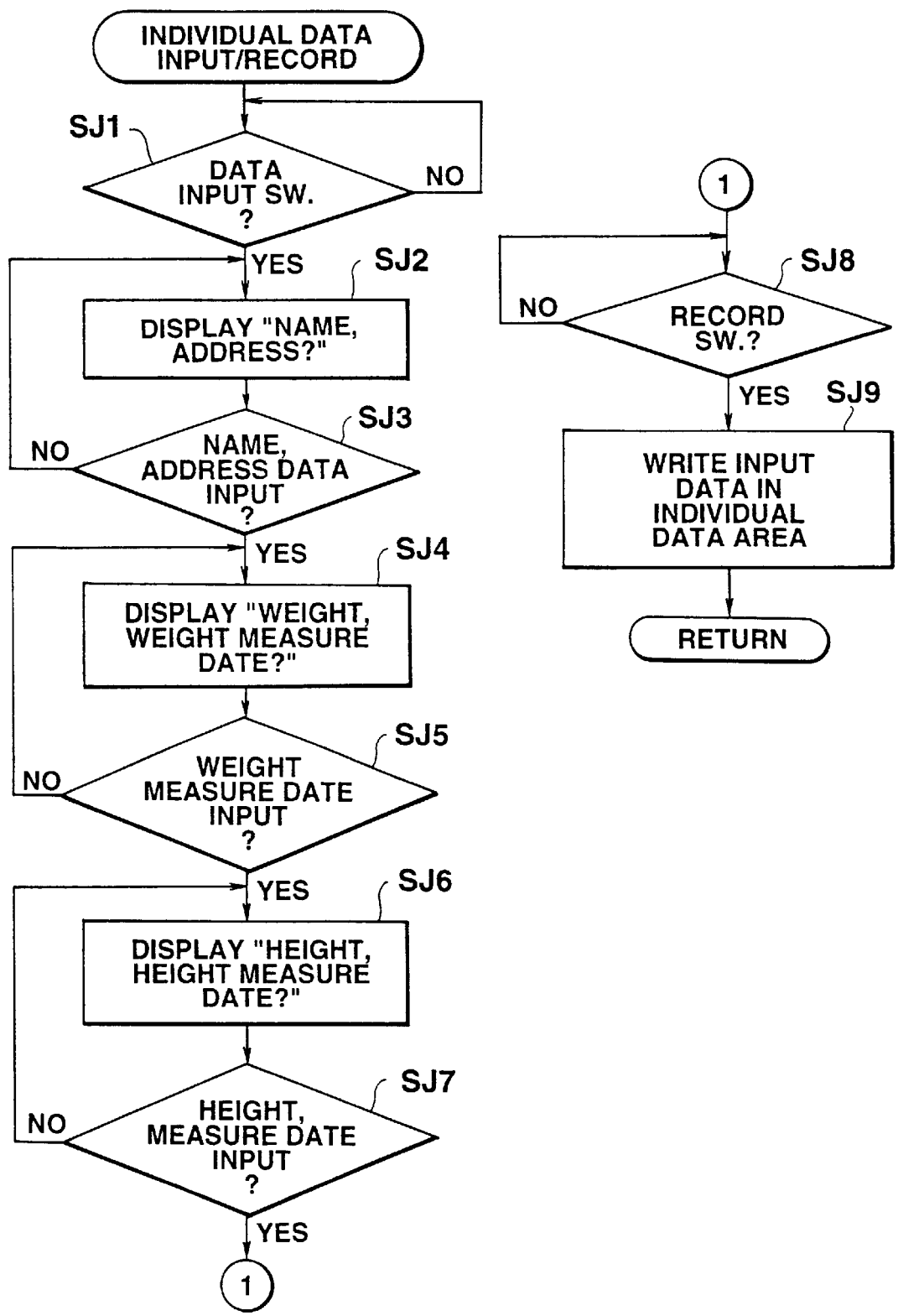
FIG. 23 is a flowchart indicative of the contents of an individual data input/record process.
Figure 24:
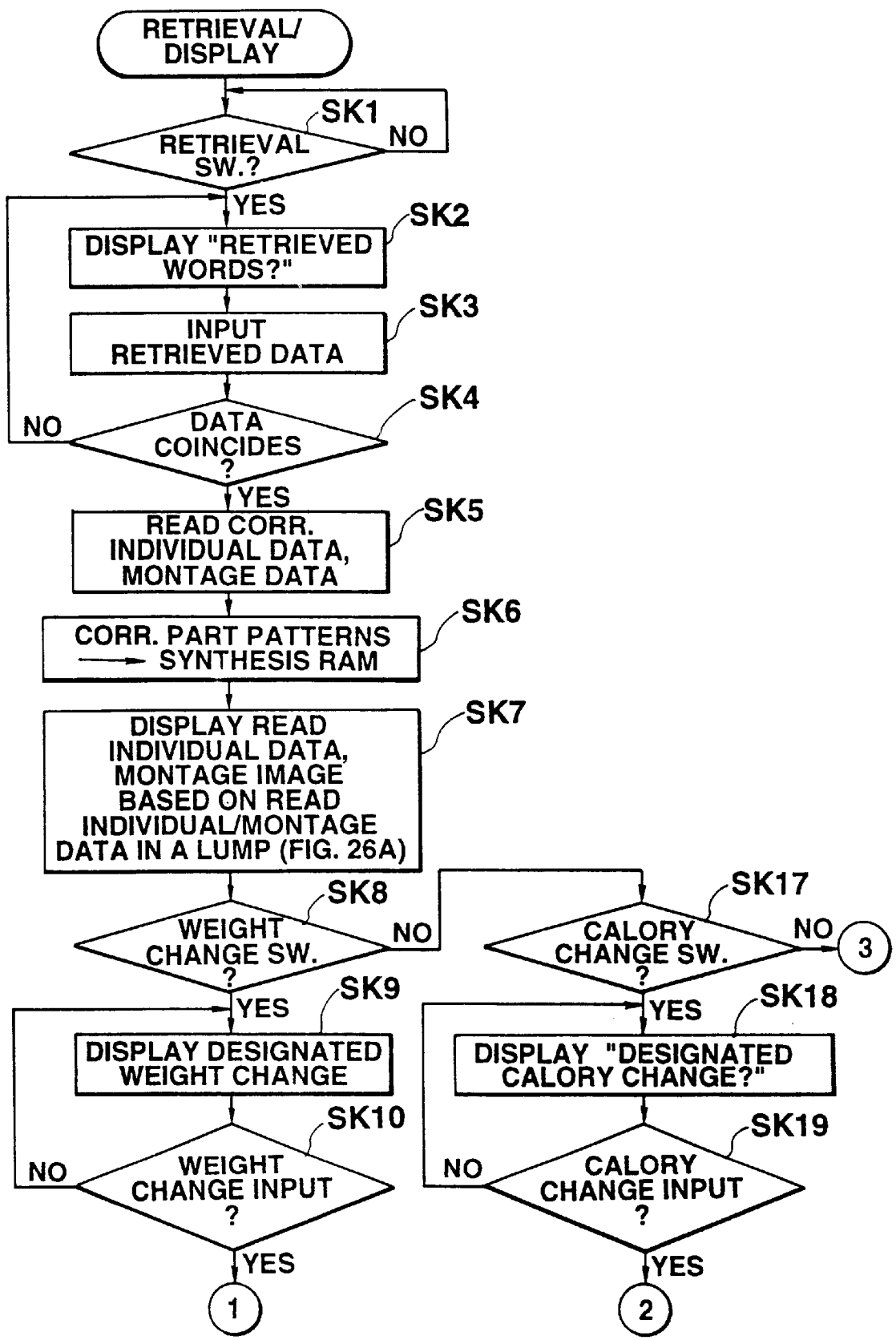
FIG. 24 is a flowchart indicative of the contents of a retrieval/record process.
Figure 25:
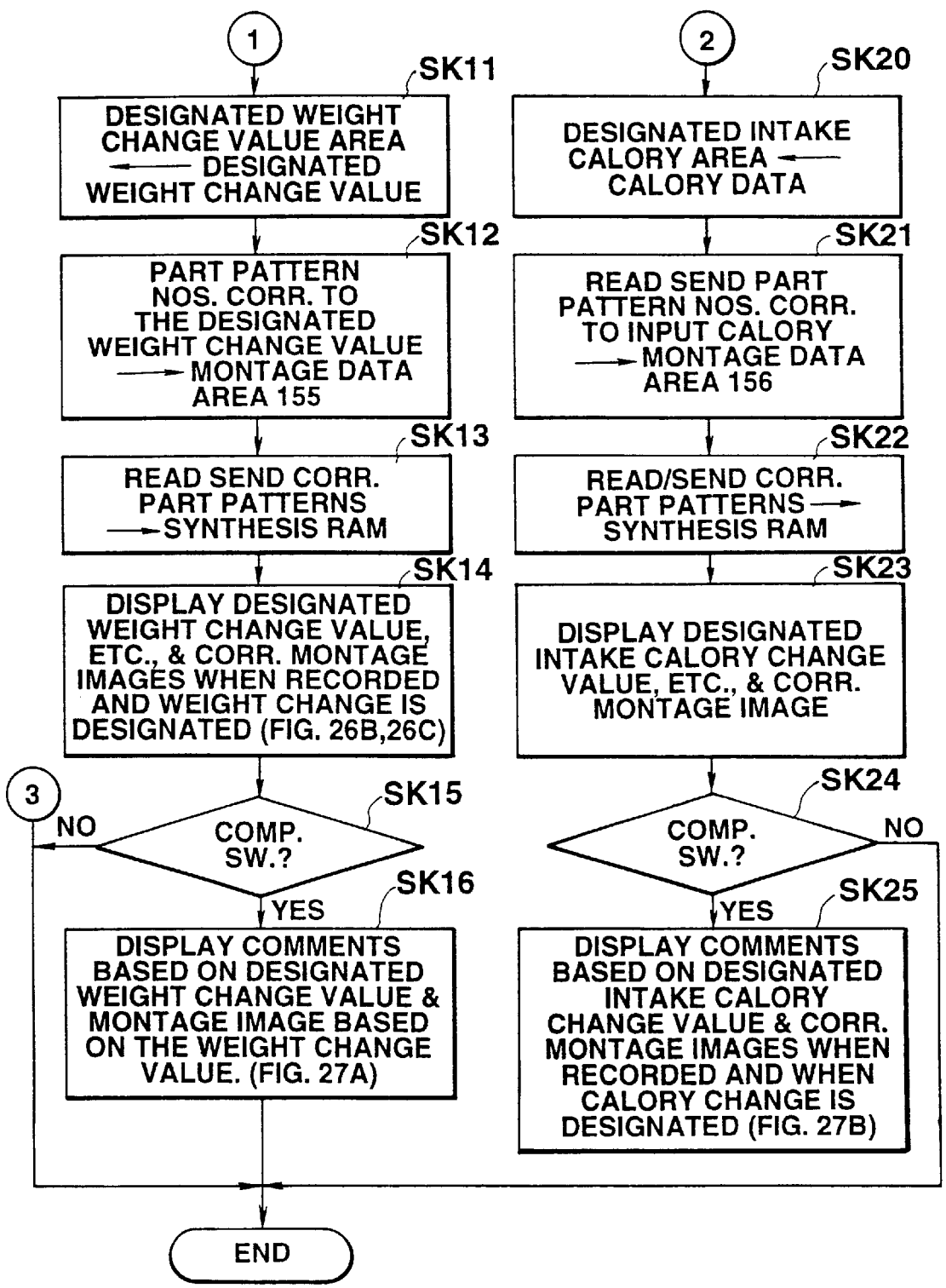
FIG. 25 is a flowchart indicative of the contents of a retrieval/record process subsequent to FIG. 24.

In the general flowchart of FIG. 22, first, an individual data (name, weight, height, etc.) input/record process of FIG. 23 is executed (step S11). A montage creation/record process of FIGS. 9 and 10 then is executed (step S12). Subsequently, a retrieval/display process of FIGS. 24 and 25 is executed (step S13).

First, the individual data inputting process at step SI1 is performed in accordance with the flow of FIG. 23. First, it is determined whether the data input switch 10 is operated (step SJ1). If so, "name, address ?" is displayed on the second display 9 (step SJ2). It is then determined whether those name, weight, etc., are input (step SJ3). A looping operation involving steps SJ2, SJ3 is repeated until inputting those data items is completed. During the repetition, the user operates the input switch 10 to input the name, weight, etc.

When it is determined at step SJ3 that inputting the name, weight, etc., is completed, "weight, weight measurement date ?" is displayed (step SJ4). It is then determined whether data on the weight and the weight measurement date is input (step Sj5). A looping operation involving steps SJ4 and SJ5 is repeated until inputting the data is completed. During the repetition, the user similarly operates the data input switch 10 to input data on the weight and weight measurement date. After those data items are input, "height, height measurement date ?" is displayed (step SJ6), and it is determined whether inputting the height and height measurement date is completed (step SJ7).

If it is determined that such required data is input, it is determined whether the record switch 6k is operated (step SJ8). If so, the data input so far is stored in the individual data area 134 of the montage data RAM 13A (step SJ9). In this case, first, the individual data input in the item "1" area of the individual data area 134 is stored therein. After this process, control returns to the general flow.

Figure 10:
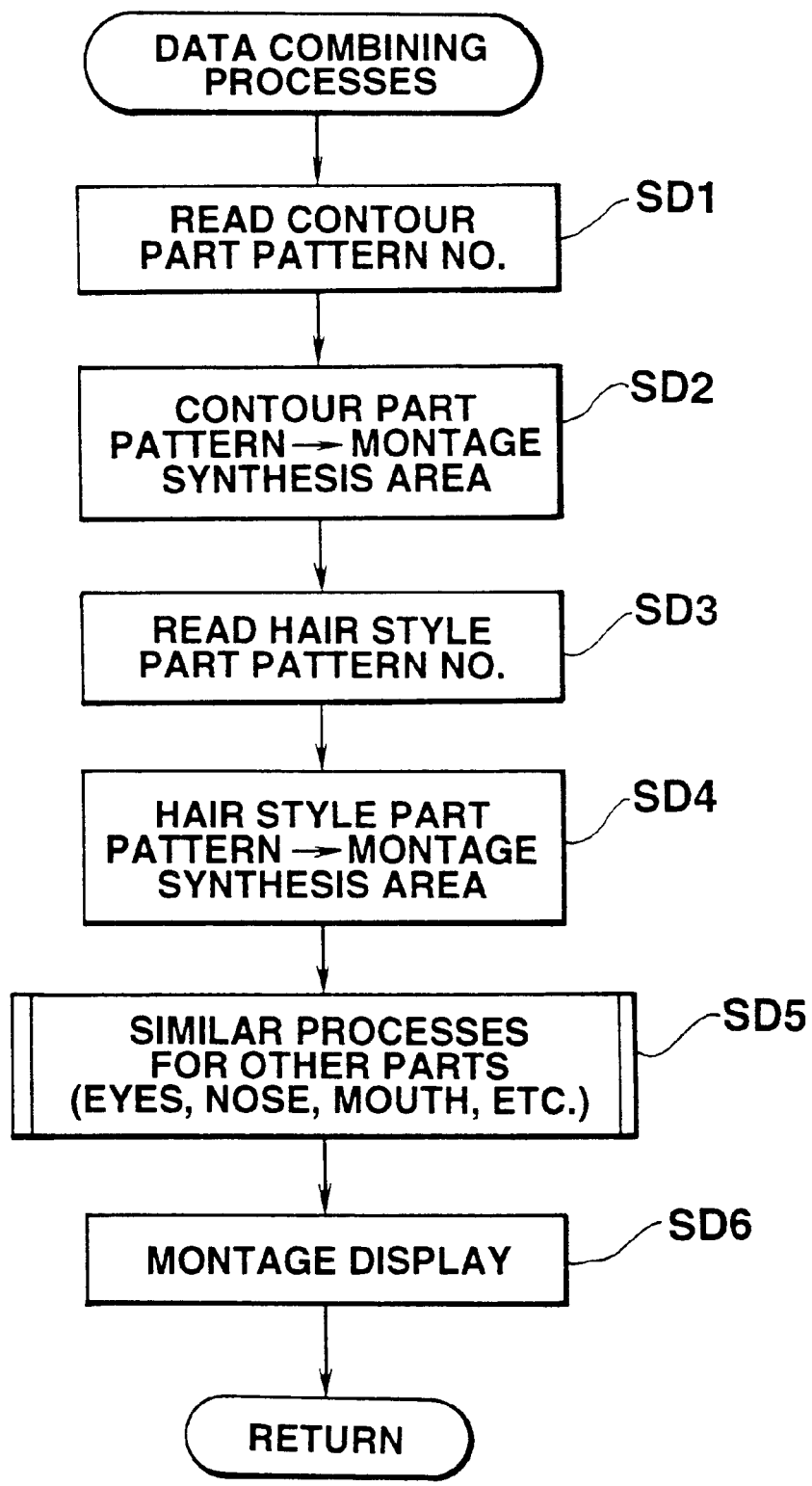
FIG. 10 is a flowchart indicative of the contents of a data combining process.

A montage creation/record process (step SI2) in the general flow of FIG. 22 is performed in the same flow as in the first embodiment of FIGS. 9 and 10. While in this case the start of the montage creation/record process in the first embodiment of FIG. 9 is made when the combined object switch 6f was operated, the start of the montage creation/record process in the second embodiment is made when the montage creation switch 26a is operated. Other processes are the same as those performed in the first embodiment of FIG. 9.

A retrieval/display process (step SI3) of the general flow is performed in accordance with the flowchart of FIG. 24.

That is, first, it is determined whether a retrieval switch 6c is operated (step SK1). If so, "Retrieved word ?" is displayed on the second display 9 (step SK2). In accordance with this display, the user operates the data input switch 10 to input as retrieval data the same data as any particular one of the names "A", "B", . . . of the individual data stored in the individual/montage data RAM 13A (step SK3).

Figure 26A:
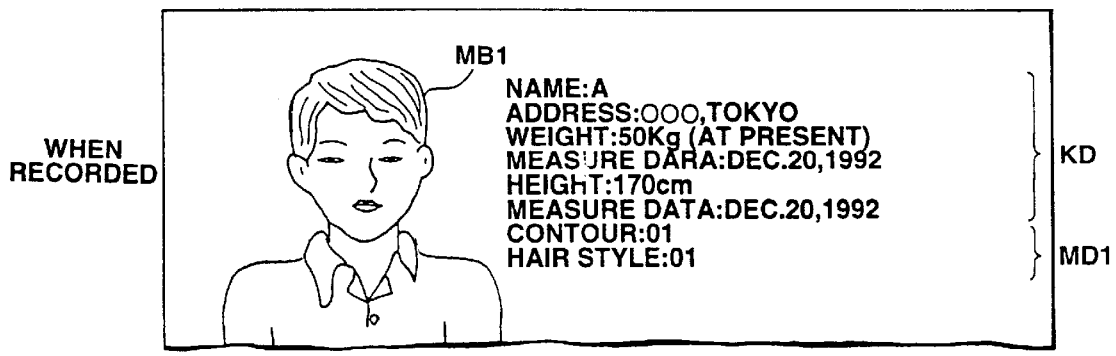
FIGS. 26A–26C illustrate displayed example of montage images of an object obtained when recorded, and its weight is increased/decreased.
Figure 26B:
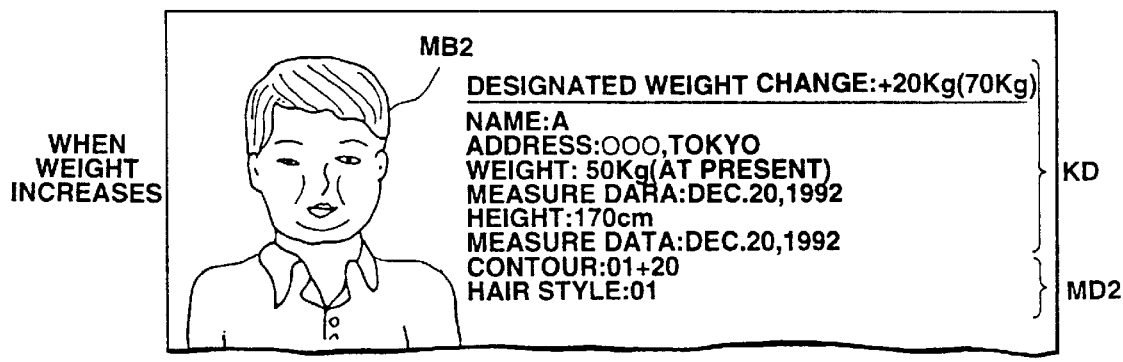

It is first determined whether the retrieved data input at step SK3 coincides with any particular name of the individual data (step SK4). When both data coincide and the name data input by the switch operation is stored at a proper location in the individual data area 134, the individual data containing the name and the corresponding montage data (the corresponding part pattern numbers) are read (step SK5). Part patterns indicated by the read part pattern number are read from the basic part pattern ROM 12B and transferred to the synthesis RAM 14 (step SK6). The read individual data and a montage image composed of combined transferred part patterns are displayed together (step SK7). For example, as illustrated in FIG. 26A, if the retrieved data relates to "A", individual data KD such as "A"'s name and address and its montage data MD1 and the "A"'s montage image MB1 are displayed together. In this display, an upper half of the "A"'s montage image is displayed and not the whole body of "A".

It is then determined whether the designated weight change switch 26d is operated (step SK8). If so, "Designated weight change value ?" is displayed (step SK9). It is then determined whether the designated weight change value is input (step SK10). It is then determined whether the user has input a weight value by the operation of the data input switch 10 in accordance with the weight display, and then that the input "weight value" is different from that stored already in the individual/montage data RAM 13A. As a result, when it is determined that the different weight value is input, an increase/decrease value as the difference between the input "weight value" and that stored already is stored as a designated weight change value in the designated weight value area 153 (step SK11 of FIG. 25). The respective part pattern numbers containing a "contour" part pattern number indicative of a "contour" part pattern corresponding to the designated weight value are stored in the montage data area 155 for weight change (step SK12).

For example, as illustrated in FIG. 21, a case will be described where the part pattern numbers "01", "01", "03", . . . are stored at the "A"'s "contour", "hair style", "eyes" part locations and "+20 Kg" is stored as the "A"'s designated weight value.

In the present embodiment, only the "contour" part pattern is changed in accordance with an increase/decrease in the weight value. Thus, only the "contour" part pattern number "01" is changed to "01+20" in accordance with the designated weight value "+20 Kg". As a result, the changed "contour" part pattern number "01+20" and other "hair style", "eyes", . . . part pattern numbers "01", "03", . . . , are stored in the montage data area 155 for weight change (step SK12).

The respective part pattern corresponding to the stored "contour" part pattern number "01+20" are read from the weight increase/decrease part pattern ROM 12D, part patterns corresponding to other "hair style", "eyes", . . . part pattern numbers "01", "03", . . . are read from the basic part pattern ROM 12B, and transferred to and combined in the synthesis RAM 14, and the resulting montage image for the designated weight change value is stored in the synthesis RAM 14 (step 13).

Figure 26C:
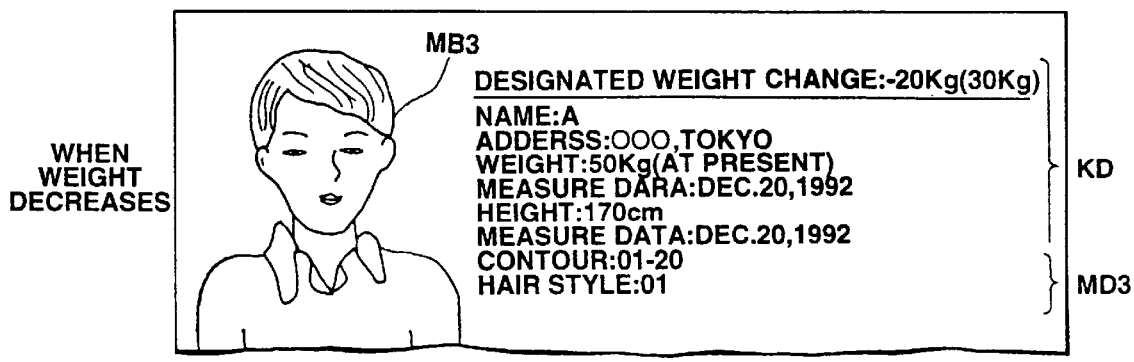

The individual data stored in the individual data area 134 is then read. Individual data KD of the appropriate person including a designated weight change value "+20 Kg" of the object (person), and the weight value "70 Kg" as the sum of the current weight value "50 Kg" and the designated weight change value "+20 Kg" on the basis of the read individual data are displayed on the first display 5 and montage data MD2 are displayed on the first display 5. Simultaneously, the part pattern numbers "01+20", "01", "03", . . . which are montage data stored in the montage data area 155 for weight change and the montage data image MB2 for the designated weight change value stored in the synthesis RAM 14 by the synthesis operation are displayed on the first display 5 (SK14). Conversely, if the designated weight change value is "−20 Kg" at steps SK13 and SK14, the individual data KD for the appropriate person including the designated weight change value "−20 Kg", and the corresponding weight value "30 Kg" and the montage data MD3 and a montage image MB3 obtained when the designated weight change value is "−20 Kg" are displayed, as shown in FIG. 26C.

As a result, displayed on the first display 5 are the montage image MB1 for the current weight value "50 Kg", a montage image MB2 imagined when the current weight value "50 Kg" increases by "+20 Kg", and a montage image MG3 imagined when the current weight value "50 Kg" decreases by "−20 Kg". Since the first display 5 can simultaneously display part names, and corresponding part pattern numbers of the montage data MD2, MD3, for example, like "contour: 01+20", "hair style: 01", the basic part pattern numbers and an increase/decrease value in the weight can be confirmed.

Subsequently, it is determined whether the comparison switch 26*f* is operated (step SK15). If not, this retrieval/display process is terminated. Thus, in this case, only a montage image MB1 and individual's data KD such as its address depending on the retrieved individual designated weight change value are displayed. If so at step SK15, a comment on the basis of the designated weight change value and the montage images MB1 and MB2 present when recorded and when a change in the weight value is designated, respectively, are displayed together (step SK16).

Figure 27:
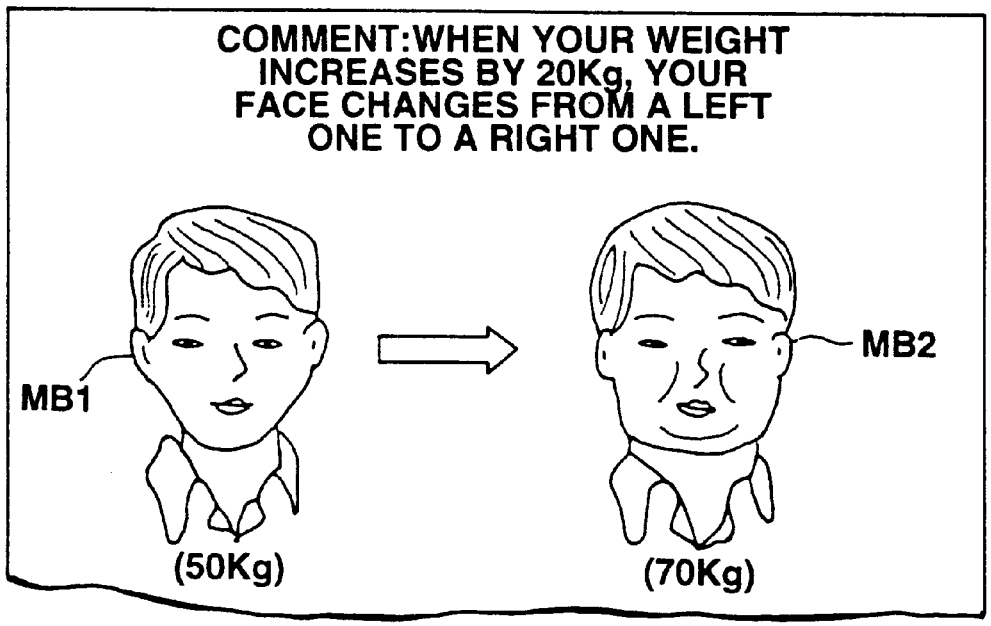
FIGS. 27A, 27B illustrate displayed further examples of montage images of an object when recorded, and when its weight is increased/decreased.
Figure 27:
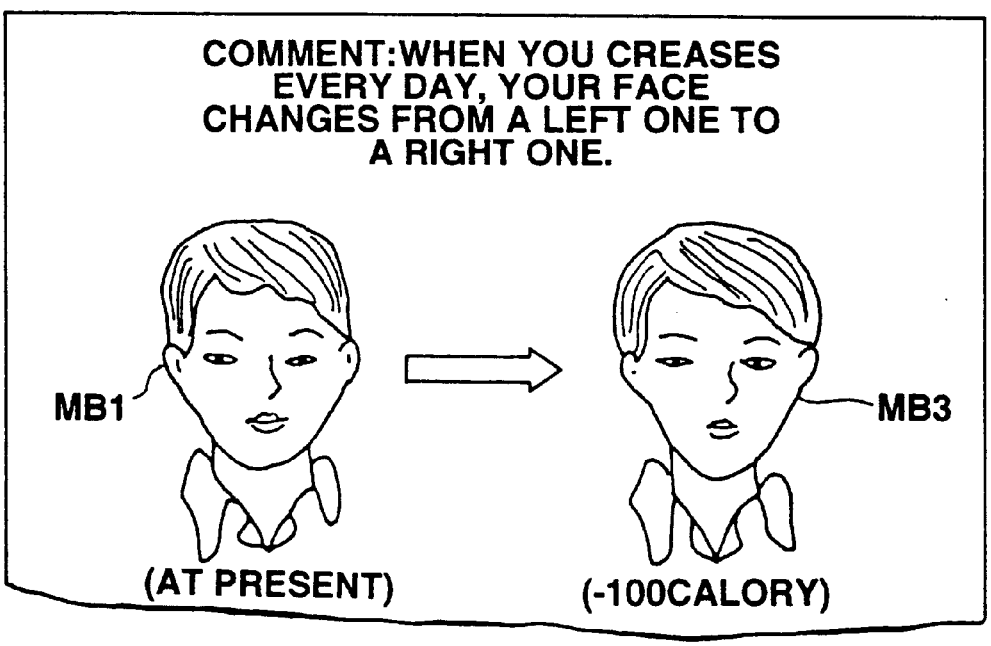

For example, when the "A"'s designated weight change value is "+20 Kg" at step SK16, a comment corresponding to the weight value stored beforehand in ROM 12 is read and displayed as "comment: when your weight increases by 20 Kg, your face changes from a left one to a right one" with the left one being a montage image MB1 present when recorded and the right one being a montage image MB2 when the weight change is designed, as shown in FIG. 27A.

When the designated weight switch 26*d* is not operated at step SK8 of FIG. 24, control passes from step SK8 to step SK17, where it is determined whether the designated intake calory switch 26*e* is operated. If so, "Designated intake calory change value?" is displayed (step SK18). It is then determined whether the data on designated intake calory change value is input (step SK19). When it is determined that the user has operated the data input switch unit 10 in accordance with the indication of the calory change value, and the calory data is input, the input calory data is stored in the designated weight change value area 153 (step SK20 of FIG. 25).

The respective part pattern numbers corresponding to the input calory change data are stored in the montage data area 156 when the intake calory change value is designated (step SK21).

For example, as shown in FIG. 21, assume that the "A"'s "contour", "hair style", "eyes", . . . part pattern numbers "01", "01", "03", etc., are stored and the "contour" part pattern number when the "A"'s intake calory change is designed is "01+20". In this case, the "contour" part pattern number is changed to "01+20" in correspondence to the calory data input this time, and the respective part pattern numbers are stored as "01+20", "01", "03", . . . in the montage data area 155 when the designated intake calory change value was designated.

The respective part patterns corresponding the stored pattern numbers are transferred to and combined in the synthesis RAM 14 (step SK22) and the synthesized montage image obtained when the intake calory change value is designated is displayed along with individual data (not shown) such as the designated intake calory change value on the first display 5 (step SK23). As a result of processes at steps SK22 and SK23, the montage image obtained when the "A" has taken in a designated intake calory change value and individual data such as designate intake calory change value at this time are displayed on the first display 5.

Subsequently, it is determined whether the comparison switch 26*f* has been operated (SK24). If not, this retrieval/display is terminated. When the designated calory switch 26*e* is operated and the comparison switch 26 is not operated, only a montage image corresponding to the retrieved individual designated intake calory change value, and its address are played. If it is determined at step SK 24 that the comparison switch 26*f* is operated, a comment on the basis of the designated intake calory change value, and the respective montage images present when recorded and when the intake calory was designated are displayed together (step SK25).

As a result of the process at step SK25, if "A"'s designated intake calory change value is, for example, "−100" calory, a comment corresponding to the weight value stored beforehand in ROM 12 is read and displayed as "comment: when you reduces 100 calories every day, your face and body shape will change from left ones to right ones", with the left ones being a montage image MB1 when recorded, and the right ones being a montage image MB2 obtained when the intake calory change value is designated, as shown in FIG. 27B.

In the second embodiment, "contour" part patterns corresponding to a designated weight change value or a designated intake calory change value are stored at intervals of 5 Kg or of given calories in the weight increase/decrease part pattern ROM 12D of FIG. 20, and only the "contour" part pattern which constitute a portion of the montage image is changed to another "contour" part pattern in accordance with the user's designated weight change value, etc. Kinds of other part patterns such as eyes, hair-style, or trunk changed depending on an increase/decrease in the weight or calory, may be stored beforehand and replaced with corresponding part patterns depending on an increase/decrease in the weight or calory to create a montage image as a combination of the obtained part patterns. In this case, when the weight increase/decrease part pattern stored in ROM 12D is for "eyes", a "single-edged eyelid" may be used if the object (person) is lightweight and thin; and a double eyelid may be used if the object (person) is fat. If the weight increase/decrease part pattern is for "hair style", a hair style pattern having a size different depending on the weight may be used. If it is for "trunk", a trunk part pattern different depending on the weight may be used. In such arrangement, not only a contour part pattern, but also other part patterns may be changed in accordance with the designated weight change value or designated intake calory change value.

While in this embodiment the display composed of LCD display means is illustrated as being used, the present invention is not limited to the particular case. For example, printing means may be used along with the display means.

While in the embodiment a person's montage image imagined when he is fat or thin is created using a designated weight increase/decrease value and an intake calory value increased/decreased from the current weight value, a person's montage image may be created and displayed which will be imagined when a change in the other data, for example, an increase or decrease in his height value occurs. A person's montage image may be created and displayed which will be imagined when a person's weight or his height is increased or decreased, using body shape data which changes depending on his ambience where food situation charges, people's kind, or the background of an age (the primitive ages-its present age).

According to the second embodiment, a montage image of an imagined face or body shape changed depending on a designated weight change or intake calory change value is created and displayed rapidly and easily. Thus, a person who is going to try dieting, a person who desires to be more fat, or a person who desires to know his possible proportion of his whole body obtained when his height increases, decreases etc., is able to view on the display his imagined face or body shape which is very useful for him. As a result, a very interesting display and a display which can be an effective stimulus to a person who wants to try dieting to achieve satisfactory dieting can be made by a simple operation.

THIRD EMBODIMENT

A third embodiment of the present invention will be described with reference to FIGS. 28–37D. The same reference numeral is used to denote the same element of the first, second and third embodiments, and further description of that element will be omitted.

Figure 28:
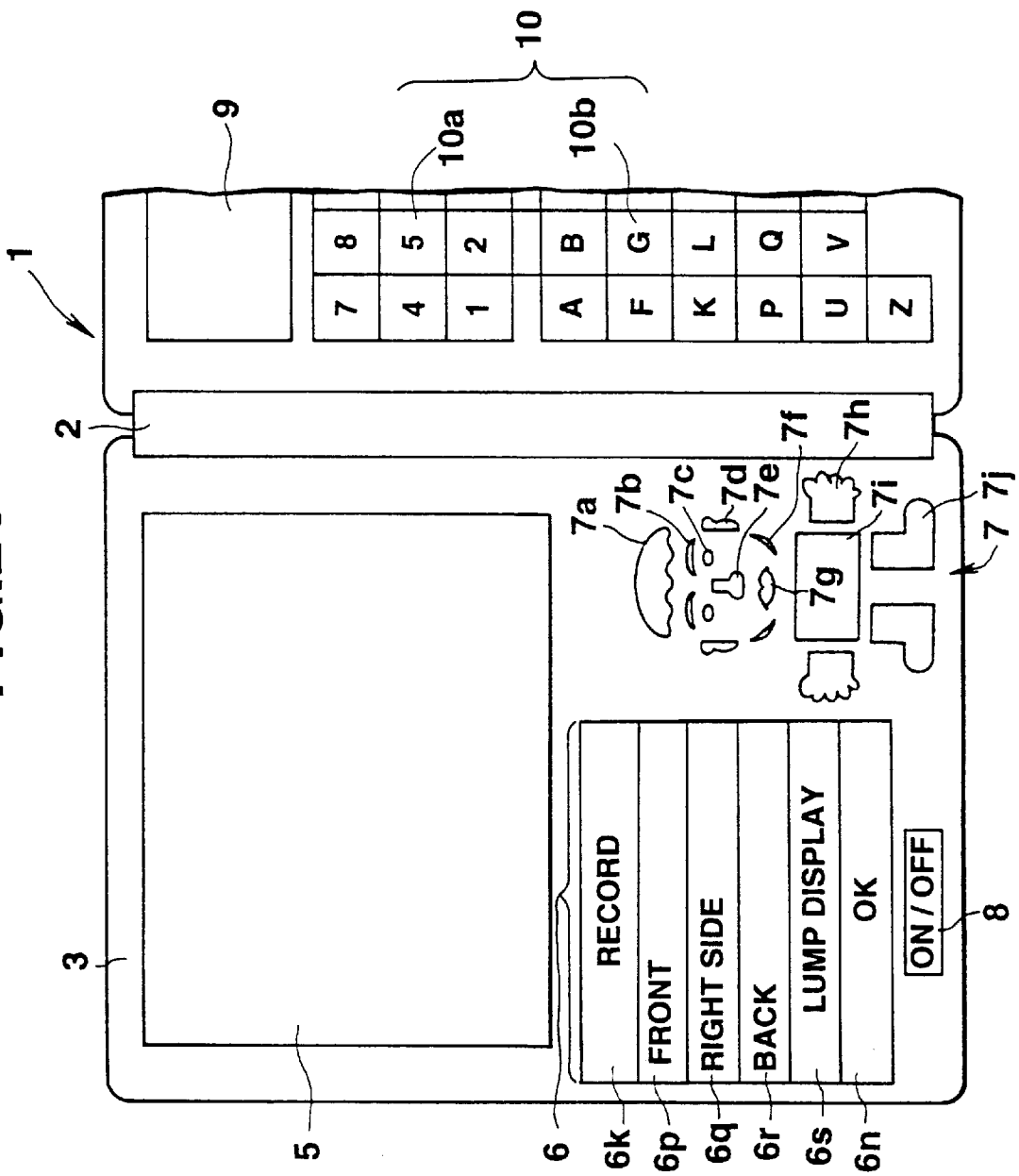
FIG. 28 is a plan view of an object image display device as a third embodiment of the present invention.

FIG. 28 shows an object image display device as the third embodiment. The object image display device 1 is provided with an item switch unit 6, an ON/OFF switch 8 for a power supply and a part switch unit 7 below the first display 5 as in the first embodiment.

The item switch unit 6 is composed of a record switch 6k, an OK switch 6n, which are similar to those of the first embodiment, a front montage switch 6p, a right side montage switch 6q, a back montage switch 6r, and a lump display switch 6s.

The part switch unit 7 is composed of a hair style, brows, eyes, ears, nose, contour, mouth, both-arms- and -hands, dress, and both-legs switches 7a, 7b, 7c, 7d, 7e, 7f, 7g, 7h, 7i and 7j as in the first embodiment.

Figure 29:
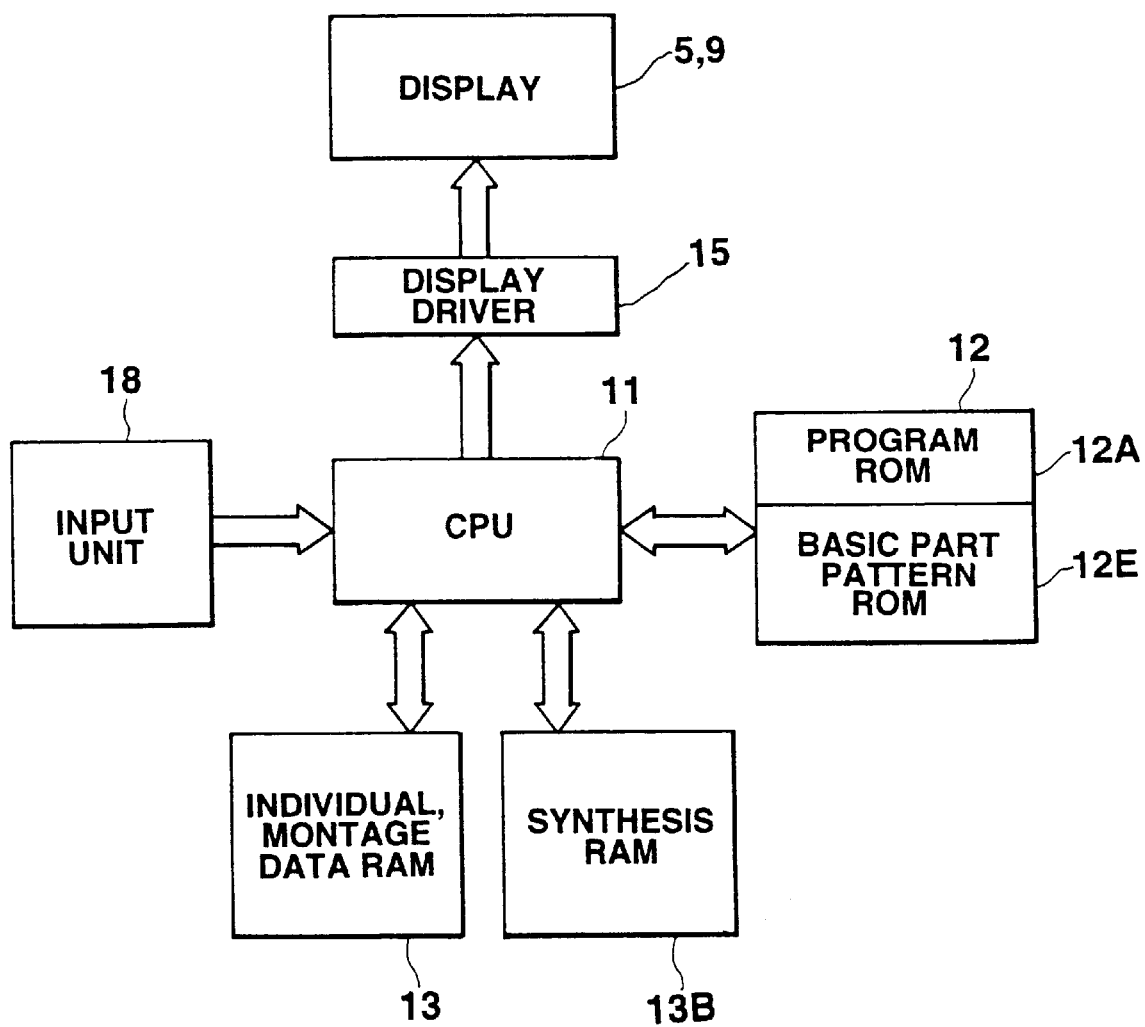
FIG. 29 is a block diagram of a whole illustrative configuration of the object image display device.

FIG. 29 is a block diagram of the object image display device, which is provided with CPU 11, ROM 12, individual/montage data RAM 13, synthesis RAM 13B, first and second displays 5, 9, display driver 15 and input unit 18, as in the first and second embodiments.

ROM 12 is provided with a basic part pattern ROM 12E of FIG. 30 in addition to a program ROM 12A. The basic part pattern ROM 12E stores a plurality of different part patterns for each of 10 kinds of parts "1"–"10" corresponding to the respective switches 7a–7j which constitute the part switch unit 7. In the case of this embodiment, the plurality of part patterns for each of the parts "1"–"10" are divided into front part patterns stored at locations corresponding to three kinds of part pattern numbers "A", "B", and "C", and 20 kinds of right side and back part patterns stored at locations corresponding to "A"-1" to "A-20" for "A", 20 kinds of right side and back part patterns stored at locations corresponding to "B"-1" to "B-20" for "B" and 20 kinds of right side and back part patterns stored at locations corresponding to "C"-1" to "C-20" for "C". For example, for "contour" front part pattern stored at the respective locations for "A"-1" to "A-20" corresponding to the "contour" part pattern number "A", a right-hand and back part patterns corresponding to the "contour" front part pattern. In this case, the respective "contour" part pattern different from those of the first and second embodiments and is composed of combined "contour", "mouth", "nose" and "ears" part patterns, "contour", "mouth", "nose" and "ears" part patterns may be prepared. The basic part pattern ROM 12E stores no left side part patterns because the left side part patterns can be created from the corresponding right side part patterns which are symmetrical with the left side part patterns.

Figure 31:
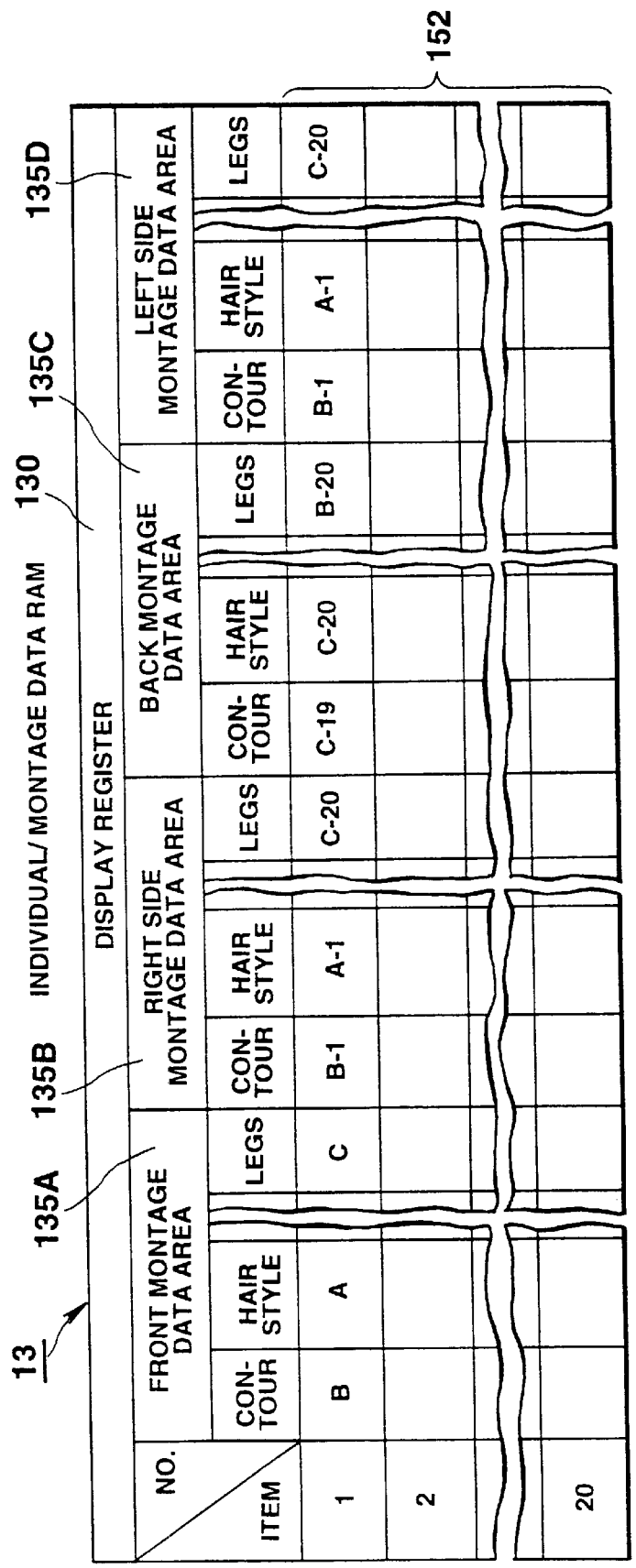
FIG. 31 shows a stored state of data in a montage ROM.

As shown in FIG. 31, the individual/montage data RAM 13 includes a display register 130, and an item data area 152 which stores 20 part pattern numbers at item locations "1"–"20". The item data area 152 includes a front montage data area 135A which stores part pattern numbers corresponding to the "contour", "hair style", . . . , "both legs" part patterns of a "front" montage; a right side montage data area 135B which stores part pattern numbers corresponding to the "contour", "hair style", . . . , "both legs" of a "right side" montage; a "back" montage data area 135C which stores part pattern numbers corresponding to the "contour", "hair style", . . . , "both legs" of a "back" montage, and a left side montage data area 135D which stores part pattern numbers of a "left side" montage.

The operation of the third embodiment will be described with reference to a flowchart of FIG. 32 and subsequent FIGURES concerned.

Figure 32:
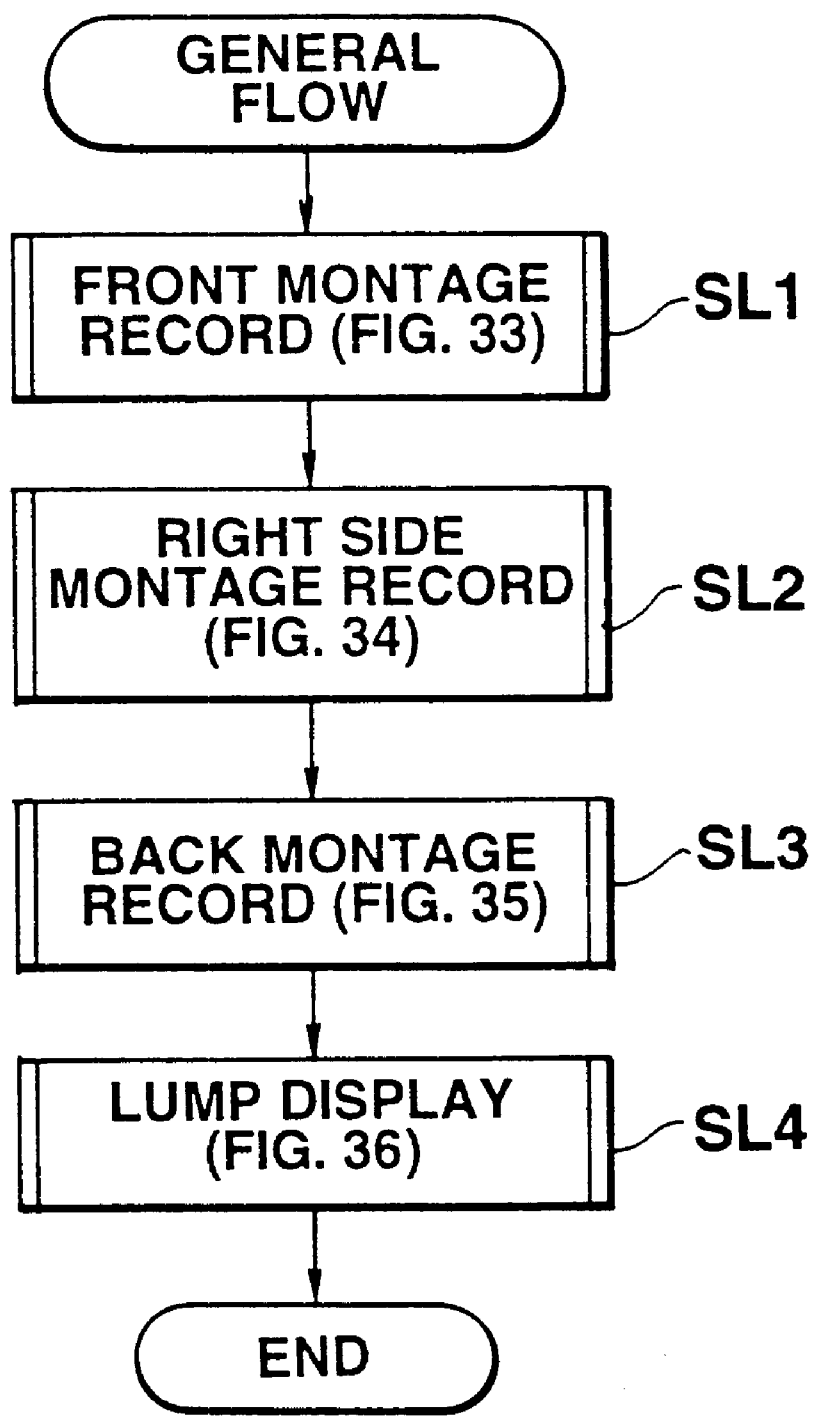
FIG. 32 is a general flow indicative of the operation of the third embodiment.
Figure 33:
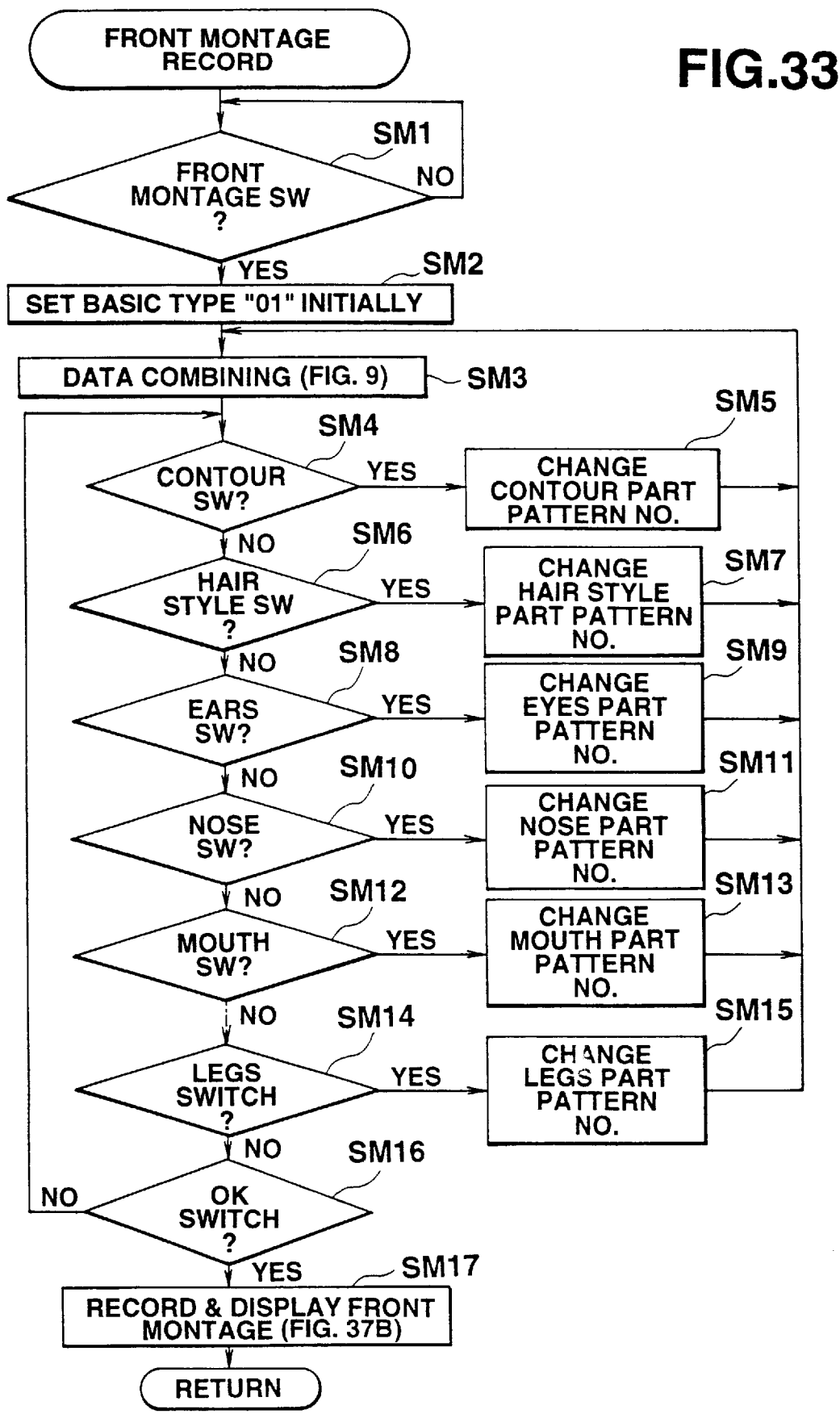
FIG. 33 is a flowchart indicative of the contents of a front montage record process.
Figure 34:
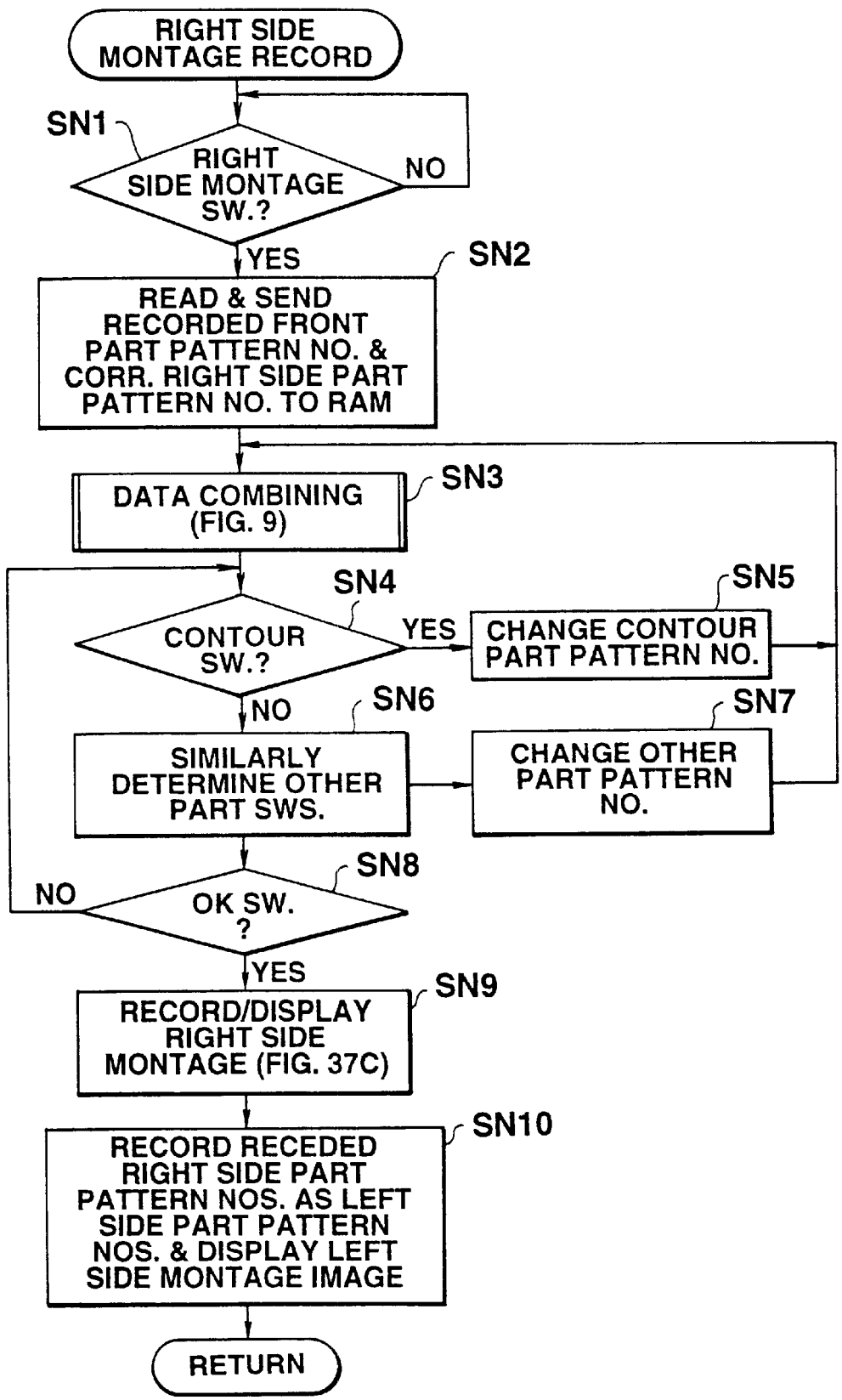
FIG. 34 is a flowchart indicative of the contents of a right side montage record process.
Figure 35:
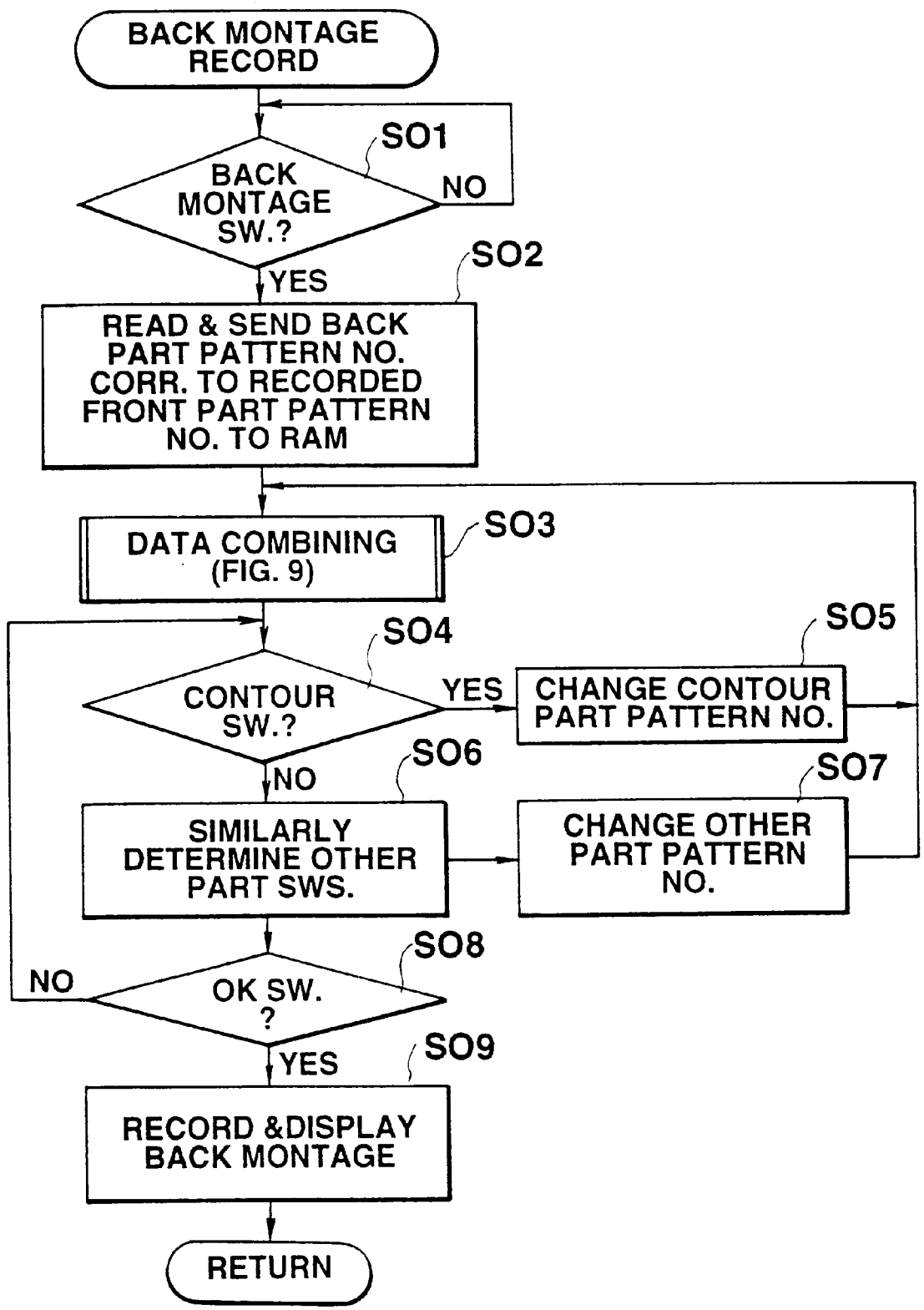
FIG. 35 is a flowchart indicative of the contents of a back montage record process.
Figure 36:
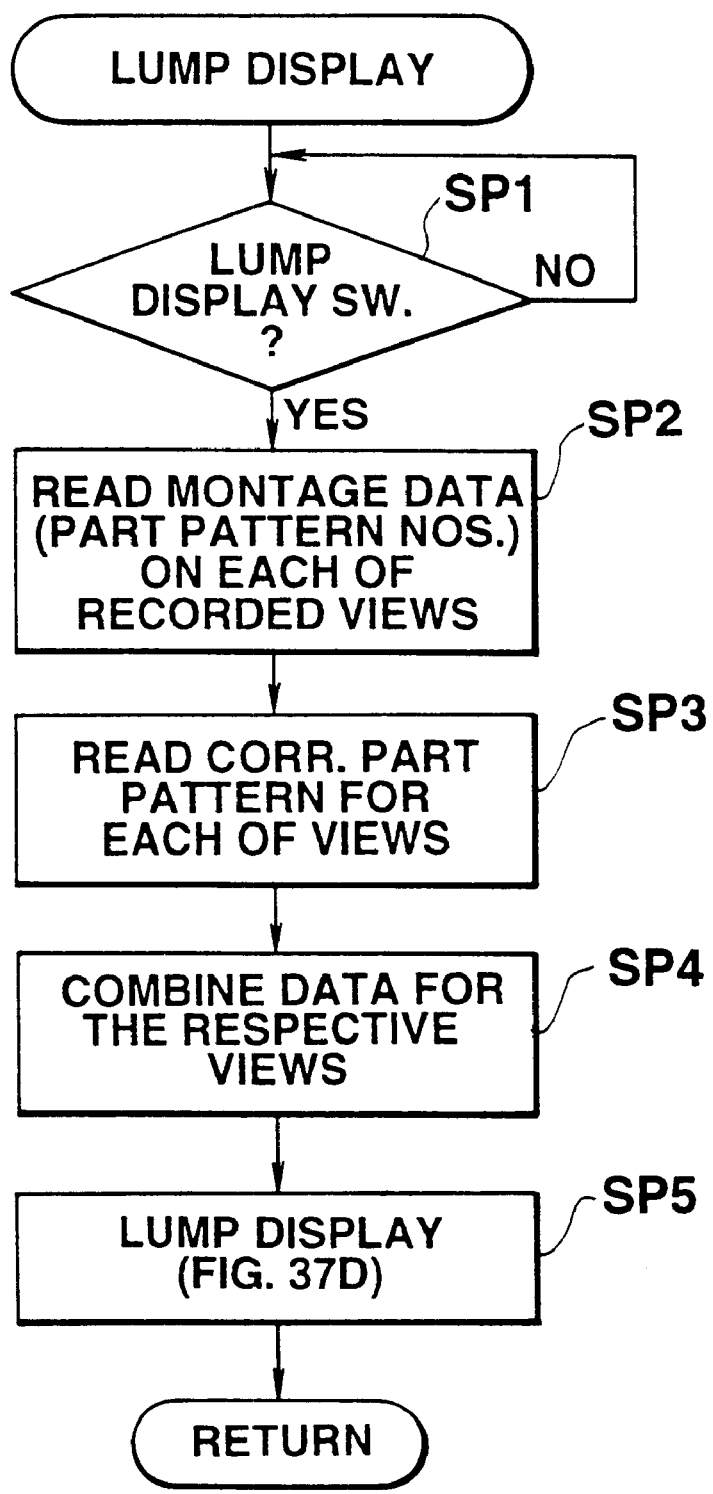
FIG. 36 is a flowchart indicative of the contents of a lump display process.
Figure 37:
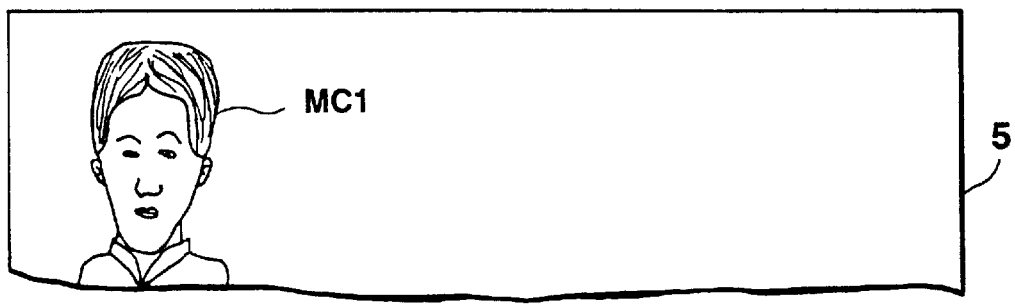
FIGS. 37A–37D illustrate displayed examples of images in the respective processes.
Figure 37:
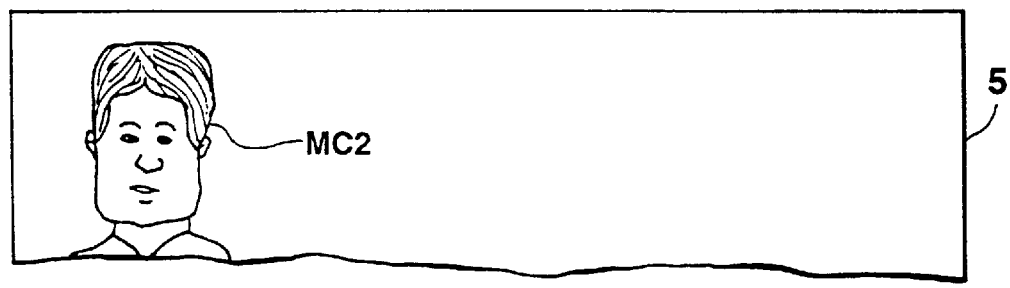
Figure 37:
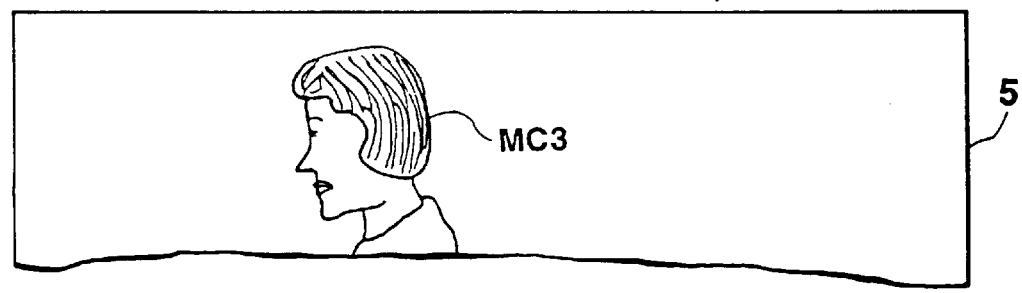
Figure 37:
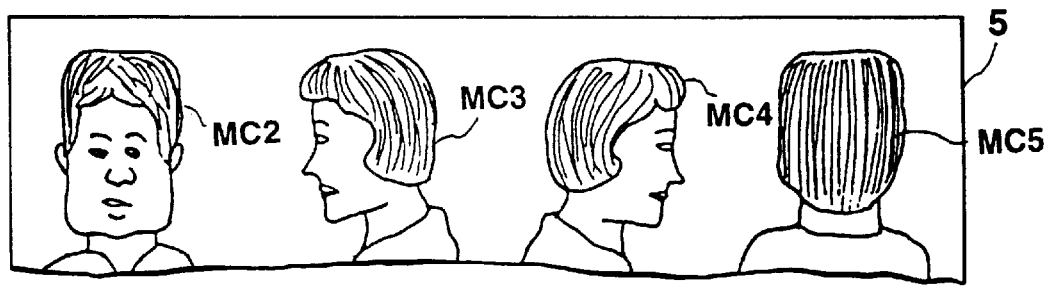

FIG. 32 is a general flow of the operation of the third embodiment, and is executed in order of a front montage record process of FIG. 33 (step SL1), a right side montage record process of FIG. 34 (step SL2), a back montage record process of FIG. 35 (step SL3), and a display process of FIG. 36 (step SL4).

First, the front montage record process is executed (step SL1) on condition that the front montage switch 6p is operated in accordance with the flow of FIG. 33 (step SM1). First, if it is determined that the front montage switch 6p is operated, a basic type "01" is set initially at step SM2 as at step SC2 of FIG. 9 for the first embodiment. As shown in FIG. 37A, by this process at step SM2, a front basic type whole-body montage image MC1 is displayed on the first display 5. The image MC1 is composed of a combination of the 10 part patterns stored at locations corresponding to "A" and having the part pattern numbers indicative of the parts "contour"-"both legs" of FIG. 30 although FIG. 37A displays only an upper portion of the montage image MC1 and not the whole body of the montage image MC1 on account of space consideration.

The processes at steps SM4–SM16 subsequent to step SM3 of FIG. 33 are executed as at steps SC3–SC16 of FIG. 9 in the first embodiment. After a front montage image MC2 (FIG. 37B) which is the same as, or similar to, the front of a desired object is displayed on the first display 5 by the process, the montage data (respective part pattern numbers) of the front montage image MC2 are recorded at the respective part locations in the front montage data area 135A and indicated by the first items "1" of the items "1"–"20" in the first item data area 152 of FIG. 31 (step SC17).

A "right side" montage record process is executed at step SL2 subsequent to step SL1 in the general flow of FIG. 32. This process is executed on condition that right side montage switch 6q is operated in accordance with the flow of FIG. 34 on condition that the right montage switch 6q is operated (step SN1). If it is determined that the right side montage switch 6q is operated, the respective right side part pattern numbers corresponding to the recorded front montage data (respective part pattern numbers) are read from the right side montage data area 135B where the data was recorded just before (SN2).

For example, if the front "contour" part pattern number "B" is recorded already as the front part pattern number, the right side part pattern number "B-1" is read as a right side part pattern number from the right side montage data area 135B corresponding to the front montage area 135A. Alternatively, the right side part pattern number "B-1" as well as other right side part pattern numbers "B-2", "B-3", . . . may be all read, combined and displayed collectively when a related montage image is synthesized and displayed, which will be described later in more detail. In this case, since many right side part patterns are displayed collectively, desired right side part patterns can be selected easily.

In this way, part pattern numbers for the right side "hair style", etc., other than the "contour" are similarly read and stored at the respective part locations in the right side montage data area 135B of the individual/data RAM 13 (step SN2).

A data combining process similar to that of FIG. 9 is executed (SN3). As shown in FIG. 37C, by this process at step SN3, a right side montage image MC3 composed of combined read right side part patterns is displayed on the first display 5. When the displayed montage image MC3 does not resemble the right side of the object, the respective switch determining steps SN4–SN7 similar to steps SM4–SM15 of FIG. 33 are executed to create a right side montage image MC3 which is the same as, or similar to, the right side of the object. If the desired right side montage image is created, the OK switch 6n is operated, so that control passes to step SN8 to step SN9, where the obtained right side montage image MC3 is displayed on the first display 5, as shown in FIG. 37C. Montage data (respective part pattern numbers) which constitutes the right side montage image MC3 is recorded in the right side montage area 135B corresponding to the item data area 152 concerned.

If the right side montage image MC3 composed of combined part patterns corresponding to the right side part pattern numbers read at step SN2 is the desired one, the OK switch 6n can be operated at once without operating the "contour" switch 7f, etc., to thereby record the part pattern numbers read automatically at step SN2 immediately at step SN9. Thus, in this case, a right side montage image composed of the part patterns corresponding to the recorded front part pattern numbers is displayed.

At step SN10 the recorded right side part pattern numbers are recorded as the left side part pattern numbers in the left side part pattern data area 135D of the individual/montage data RAM 13 (step SN10).

Since the right and left side montage images are symmetrical with each other, the part pattern numbers for the left side are recorded as such at the respective part locations of the data area 135D. A right side montage image is synthesized in the synthesis RAM 13B on the basis of the corresponding recorded left side part pattern numbers, is inverted so as to obtain a corresponding left side montage image MC4, which is recorded at another location in the synthesis RAM 13B and is displayed (FIG. 37D).

At step SL3 subsequent to step SL2 of the general flow, a back montage record process is executed, which is executed in accordance with the flowchart of FIG. 35 on condition that the back montage switch 6r is operated (step SO1). If it is determined that the back montage switch 6r is operated, a back part number, for example, of "C-20", corresponding to the recorded front part pattern number is read (step SO2). Similarly, other back part pattern numbers for "hair style", etc., are read and stored at respective locations in the back montage area 135C.

At step SO3 data combining process similar to that of FIG. 9 is executed. At step SO3 a whole-body back montage image MC5 composed of the respective read back part patterns is displayed on the first display 5, as shown in FIG. 37D. The back montage MC5 displayed on the first display 5 does not resemble the back of a desired object, processes similar to those at step SM4–SM15 of FIG. 33 are executed at steps SO4–SO7 to create a montage image which is the same as, or similar to, the desired object. When the desired right side montage image is created, the OK switch 6n is operated. This causes control to pass from step SO8 to step SO9, where the resulting back montage image MC5 is displayed on the first display 5, and the respective part pattern numbers for the back montage image are recorded in the back montage area 135C corresponding to the item data area 152 concerned.

If the back montage image composed of combined part patterns corresponding to the back part pattern numbers read at step SO2 is the desired montage one, the OK switch 6n can be operated at once without operating the "contour" switch 7f, etc., to record the part pattern numbers (as read at step SO2) at step SN9. Thus, in this case, the back montage switch 6r and then the OK switch 6n are only operated to display the back montage image MC5 corresponding to the front montage image MC2.

At step SL4 subsequent to step SL3 of the general flow a lump display process is executed on condition that the lump display switch 6s has been operated in accordance with the flow of FIG. 36 (step SP1). If it is determined that the lump display switch 6s has been operated, data on the respective recorded montages (part pattern numbers) on the respective views are read (SP2).

That is, when it is determined that the lump display switch 6s is operated in a state where an object data on which is recorded in the item "1" of FIG. 31 is beforehand designated, the part pattern numbers stored in the front montage data area 135A, right side montage data area 135B and back montage data area 135C for the item "1" are read, and the left side part pattern numbers recorded in the left side montage area 135D at step SN10 of FIG. 34 are read separately.

Thereafter, part patterns corresponding to the respective read part pattern numbers are read for each of the front, right side, left side and back from the ROM 12D (step SP3). The read part patterns for each of the front, right side, left side and back are combined (step SP4). The respective resulting montage images MC2–MC5 for the respective front, right side, left side and back are displayed in a lump on the first display 5 (step SP5). In this case, for a left montage MC5, the montage image MC3 composed of combined right side part patterns is once inverted with reference to right and left in a process such as is shown at step SN10 and the resulting montage image is stored in the synthesis RAM 13B and displayed as such.

While in the third embodiment the montage images MC2–MC5 are displayed on the display 5, the respective montage images may be printed out simultaneously with display of such images or without such display.

While in the third embodiment the four front, right side, left side, and back montage images are illustrated as being displayed on the display 5, a plan view montage image may be displayed. Alternatively, a montage image viewed from a different angle, for example, an intermediate side montage image formed between the front and right side montage images may be displayed. In this case, a plurality of kinds of part patterns for the parts of each of a plan view montage image and an intermediate side montage image is required to be stored beforehand in the basic part pattern ROM 12E.

According to the third embodiment, if the part patterns on at least one of any views are designated for the respective parts, at least one part pattern is automatically selected for each of the parts of another view corresponding to those designated part patterns. Thus, when a montage image composed of combined part patterns which constitute any one view is created, it is not required to start to search and select with a clear slant the respective part patterns of a different view corresponding to that view and a corresponding montage image on the different view is created and displayed rapidly and easily.

According to the third embodiment, a montage image on one of the right and left sides is created on the basis of the respective part patterns for the parts which constitute a montage image on the other of the right and left sides. Thus, both the right and left side part patterns are not required to be stored. That is, only one-side part patterns are required to be stored and hence the capacity of the memory for the part patterns is greatly reduced.

What is claimed is:

1. A portable image display control device to be carried with a user comprising:
    random access memory type first storage means for storing a first living thing image corresponding to a predetermined face or body of a living thing;
    liquid crystal type display means for displaying living thing images;
    first display control means for controlling said liquid crystal type display means to display the first living thing image stored in said random access memory type first storage means;
    data input means to be operated by the user to input change control data for changing the first living thing image being displayed on said display means;
    random access memory type second storage means for storing the change control data input by said data input means; and
    second display control means for controlling said liquid crystal type display means to display another second living thing image whose body shape differs from a body shape of the first living thing image being displayed on said liquid crystal type display means in accordance with values represented by the change control data stored in said random access memory type second storage means.

2. The portable image display control device according to claim 1, further comprising:
    name input means for inputting name data of said first living thing image; and
    third storage means for storing the name data input by said name input means, wherein said first display control means controls said liquid crystal type display means to display the name data stored on said third storage means.

3. The portable image display control device according to claim 1, further comprising:
    operation means operated by the user;
    comment display control means for controlling said liquid crystal type display means to display comments regarding changes in body shape between said first and second living thing images.

4. The portable image display control device according to claim 1, wherein said second living thing image is an image of at least one of a fattened or thinned face or body of said first living thing image.

5. The portable image display control device according to claim 1, wherein said change control data includes at least one of weight data, height data, and calorie data.

6. The portable image display control device according to claim 1, wherein said living thing images comprise images of a human or an animal.

7. The portable image display control device according to claim 1, wherein said living thing images comprise a plurality of partial images.

8. The portable image display control device according to claim 1, wherein said data input means comprises keys.

9. The portable image display control device according to claim 1, wherein said body comprises a whole body including said face.

10. The portable image display control device according to claim 1, wherein at least a part of said first living thing image comprises substantially all of said face or body, or a part of said face or body.

11. A portable image display control device to be carried with a user comprising:
    random access memory type first storage means for storing a first living thing image corresponding to a predetermined face or body of a living thing;
    liquid crystal type display means for displaying living thing images;
    first display control means for controlling said liquid crystal type display means to display the first living thing image stored in said random access memory type first storage means;
    calorie data input means for allowing the user to input calorie data;

random access memory type second storage means for storing the calorie data input by said data input means;

second display control means for controlling said liquid crystal type display means to display the calorie data stored in said random access memory type second storage means; and third display control means for controlling said liquid crystal type display means to display another second living thing image whose body shape differs from a body shape of the first living thing image being displayed, in accordance with a value represented by the input calorie data.

12. The portable image display control device according to claim 11, further comprising:

name input means for inputting name data of said first living thing image; and third storage means for storing the name data input by said name input means, wherein said first display control means controls said liquid crystal type display means to display the name data stored in said third storage means.

13. The portable image display control device according to claim 11, further comprising:

operation means operated by the user;

comment display control means for controlling said liquid crystal type display means to display comments regarding changes in body shape between said first and second living thing images.

14. The portable image display control device according to claim 11, wherein said second living thing image is an image of at least one of a fattened or thinned face or body of said first living thing image.

15. The portable image display control device according to claim 11, wherein said calorie data is intake calorie data.

16. The portable image display control device according to claim 11, wherein said living thing images comprise images of a human or an animal.

17. The portable image display control device according to claim 11, wherein each of said living thing images comprises a plurality of partial images.

18. The portable image display control device according to claim 11, wherein said calorie data input means comprises keys.

19. The portable image display control device according to claim 11, wherein said body comprises a whole body including said face.

20. The portable image display control device according to claim 11, wherein at least a part of said first living thing image comprises substantially all of said face or body, or a part of said face or body.

21. A portable image display control device to be carried with a user comprising:

random access memory type first storage means for storing a first living thing image corresponding to a predetermined face or body of a living thing;

liquid crystal type display means for displaying living thing images and weight data;

first display control means for controlling said liquid crystal type display means to display the first living thing image stored in said random access memory type first storage means and weight data of the first living thing image;

weight data input means for allowing the user to input weight data;

random access memory type second storage means for storing the weight value data input by said weight data input means; and second display control means for controlling said liquid crystal type display means to display another second living thing image whose body shape differs from the first living thing image being displayed on said display means in accordance with a value represented by said weight data stored in said second storage means.

22. The portable image display control device according to claim 21, further comprising:

name input means for inputting name data of said first living thing image; and third storage means for storing the name data input by said name input means, wherein said first display control means controls said liquid crystal type display means to display the name data stored in said third storage means.

23. The portable image display control device according to claim 21, further comprising:

operation means operated by the user;

comment display control means for controlling said liquid crystal type display means to display comments regarding changes in body shape between said first and second living thing images when said operation means is operated.

24. The portable image display control device according to claim 21, wherein said second living thing image is an image of at least one of a fattened or thinned face or body of said first living thing image.

25. The portable image display control device according to claim 21, wherein said weight data indicates an actual weight data of the first living thing image, or an indication of an increase or decrease in the actual weight data.

26. The portable image display control device according to claim 21, wherein said living thing images include images of a human or an animal.

27. The portable image display control device according to claim 21, wherein each of said living thing images comprises a plurality of partial images.

28. The portable image display control device according to claim 21, wherein said weight data input means comprises keys.

29. The portable image display control device according to claim 21, wherein said body comprises a whole body including said face.

30. The portable image display control device according to claim 21, wherein at least a part of said first living thing image comprises substantially all of said face or body, or a part of said face or body.

31. An image display control method for displaying living thing images on a portable image display control device to be carried with a user, comprising:

a first display control step of controlling random access memory type storage means for storing a first living thing image corresponding to a predetermined face or body of a living thing, and controlling a liquid crystal type display means to display said first living thing image stored in said random access memory type storage means;

a data input step of allowing the user to input change control data for changing a body shape of a displayed living thing image;

a storing step of storing the change control data input during said data input step; and a second display control step of controlling said liquid crystal type display means to display another second living thing image whose body shape differs from a body shape of the first living thing image being displayed on said liquid crystal type display means in accordance with values represented by the change control data stored during said storage step.

32. The image display control method according to claim 31, further comprising:

an operating step of operating operation means; and comment display control step of controlling said liquid crystal type display means to display comments corresponding to changes in body shape between said first and second living thing images when said operation means is operated.

33. The image display control method according to claim 31, wherein said second living thing image is an image of at least one of a fattened or thinned face or body of said first living thing image.

34. The image display control method according to claim 31, wherein said living thing images include images of a human or an animal.

35. The display control method according to claim 31, wherein each of said living thing images comprises a plurality of partial images.

36. The image display control method according to claim 31, wherein said body comprises a whole body including said face.

37. The image display control method according to claim 31, wherein at least a part of said first living thing image comprises substantially all of said face or body, or at least a part of said face or body.

38. An image display control method for displaying living thing images on a portable image display control device to be carried with a user, comprising:

a first display control step of controlling random access memory type storage means for storing a first living thing image, and of controlling liquid crystal type display means to display said first living thing image stored in said random access memory type storage means;

a calorie data input step of allowing the user to input calorie data;

a storing step of storing the calorie data input during said calorie data input step;

a second display control step of controlling said liquid crystal type display means to display the calorie data stored during said storing step; and a third display control step of controlling said liquid crystal type display means to display another second living thing image whose body shape differs from a body shape of said first living thing image being displayed in accordance with a value represented by the calorie data input during said calorie data input step.

39. The image display control method according to claim 38, further comprising:

an operating step of operating operation means; and comment display control step of controlling said liquid crystal type display means to display comments corresponding to changes in body shape between said first and second living thing images when said operation means is operated.

40. The image display control method according to claim 38, wherein said second living thing image is an image of at least one of a fattened or thinned face or body of said first living thing image.

41. The image display control method according to claim 38, wherein said calorie data is intake calorie data.

42. The image display control method according to claim 38, wherein said living thing images include images of a human or an animal.

43. The display control method according to claim 38, wherein each of said living thing images comprises a plurality of partial images.

44. The image display control method according to claim 38, wherein said body comprises a whole body including said face.

45. The image display control method according to claim 38, wherein at least a part of said first living thing image comprises substantially all of said face or body, or at least a part of said face or body.

46. An image display control method for displaying living thing images on a portable image display control device to be carried with a user, comprising:

a first display control step of controlling random access memory type storage means for storing a first living thing image and weight data thereof, and of controlling liquid crystal type display means to display said first living thing image and the weight data thereof stored in said storage means;

a weight data input step of allowing the user to input weight data;

a storing step of storing the weight data input during said weight data input step; and a second display control step of controlling said liquid crystal type display means to display another second living thing image whose body shape differs from a body shape of said first living thing image being displayed on said liquid crystal type display means in accordance with a value represented by the weight data stored during said storing step.

47. The image display control method according to claim 46, further comprising:

an operating step of operating operation means; and comment display control step of controlling said liquid crystal type display means to display comments corresponding to changes in body shape between said first and second living thing images when said operation means is operated.

48. The image display control method according to claim 46, wherein said second living thing image is an image of at least one of a fattened or thinned face or body of said first living thing image.

49. The image display control method according to claim 46, wherein said weight data indicates an actual weight value of the first living thing image, or an indication of an increase or decrease in the actual weight.

50. The image display control method according to claim 46, wherein said living thing images include images of a human or an animal.

51. The display control method according to claim 46, wherein each of said living thing images comprises a plurality of partial images.

52. The image display control method according to claim 46, wherein said body comprises a whole body including said face.

53. The image display control method according to claim 46, wherein at least a part of said first living thing image comprises substantially all of said face or body, or at least a part of said face or body.

54. A computer readable recording medium storing a control program for controlling a portable image display control device to be carried with a user, to display a first living thing image corresponding to a predetermined face or body of a living thing and a second living thing image, said control program makes a computer;

control random access memory type storage means to store said first living thing image;

control liquid crystal type display means to display the first living thing image;

store change control data input by the user on a random access memory; and control said liquid crystal type display means to display a second living thing image whose body shape differs from a body shape of the first living thing image being displayed, in accordance with values represented by the change control data.

55. A computer readable recording medium storing a control program for controlling a portable image display control device to be carried with a user, to display a first living thing image corresponding to a predetermined face or body of a living thing and a second living thing image, said control program makes a computer;

control random access memory type storage means to store said first living thing image;

control liquid crystal type display means to display the first living thing image;

store calorie data input by the user on a random access memory; and control said liquid crystal type display means to display a second living thing image whose body shape differs from a body shape of the first living thing image being displayed, in accordance with a value represented by the input calorie data.

56. A computer readable recording medium storing a control program for controlling a portable image display control device to be carried with a user, to display a first living thing image corresponding to a predetermined face or body of a living thing and a second living thing image, said control program makes a computer;

control random access memory type storage means to store said first living thing image and weight value data thereof;

control liquid crystal type display means to display the first living thing image and the weight value data thereof;

store weight value data on a random access memory when the weight value data are input by the user; and control said liquid crystal type display means to display a second living thing image whose body shape differs from a body shape of the first living thing image being displayed, in accordance with a value represented by the stored weight value data.

57. An image display control device which controls a display unit to display a living thing image formed by assembling a plurality of part images stored in a part image memory, comprising:

data storage means for storing designation data for designating the part images of the living thing image being displayed on said display unit, and personal data indicating at least name and phone number relating to the living thing image, wherein the stored designation data and personal data are associated with each other, and display control means for searching said data storage means for the personal data based on inputted search data, for reading out part images designated by the designation data corresponding to the personal data from said part image storage memory when the personal data which coincide with the inputted search data is found, and for controlling said display unit to display a living-thing image formed by assembling said read-out part images.

58. The image display control device according to claim 57 further comprising print means for printing the living thing image, or the living thing image with the personal data.

59. The image display control device according to claim 57, wherein the personal data indicate any one of name, address, phone number, age, or height corresponding to the living thing image.

60. The image display control device according to claim 57, wherein the living thing image includes not only a human being image but also images of other living things such as animal images and botanical images.

61. The image display control device according to claim 57, wherein the living thing image is an image representing a face or an image representing a whole body.

62. The image display control device according to claim 57, wherein said data storage means comprises storage means for storing at least one of document data and palm line data corresponding to the living thing image, in addition to the personal data and the designation data.

63. The image display control device according to claim 57, further comprising replacement control means for replacing at least one part image of the part images of the living thing image with the other part image stored in and said part image storage means, and for controlling said display unit to display the living thing image whose part image has been replaced, in order to modify at least a part of the living thing image being displayed on said display unit under control of said display control means.

64. An image display control device which controls a display unit to display a living thing image formed by assembling a plurality of part images stored in a part image memory, comprising:

data storage means for storing designation data for designating the part images of the living thing image being displayed on said display unit, and personal data indicating at least name and phone number relating to the living thing image, wherein the stored designation data and personal data are associated with each other, and display control means for searching said data storage means for the personal data based on inputted search data, for reading out part images designated by the designation data corresponding to the personal data from said part image storage memory when the personal data which coincide with the inputted search data is found, and for controlling said display unit to display a living thing image formed by assembling said read-out part images and the found personal data.

65. An image display control device which controls a display unit to display a plurality of living thing images each formed by assembling a plurality of part images stored in a part image memory, comprising:

data storage means for storing data; and storage control means for controlling said data storage means to store plural sets of designation data for designating the part images of each living thing image, and plural sets of personal data each including name and phone number relating to the plurality of the living thing images, while associating the designation data and the personal data with each other, before the plurality of living thing images are displayed on said display unit.

66. The image display control device according to claim 65, further comprising display control means for searching said data storage means for the personal data based on inputted search data, for reading out part images designated by the designation data corresponding to the personal data from said part image storage memory when the personal data which coincide with the inputted search data is found, and for controlling said display unit to display a living thing image formed by assembling said read-out part images and the found personal data.

67. The image display control device according to claim 65, further comprising display control means for reading out plural sets of part images designated by the plurality of designation data sets corresponding to the plurality of personal data sets stored in said data storage means from said part image storage means, and for controlling said display unit to collectively display a plurality of living thing images each of which is formed by assembling the read-out part images.

68. An image display control method for controlling a display unit to display a living thing image formed by assembling a plurality of part images stored in part image storage means, comprising: data storing step of storing designation data for designating the part images of the living thing image being displayed on said display unit, and personal data indicating at least name and phone number relating to the living thing image, wherein the stored designation data and personal data are associated with each other, and display controlling step of searching data stored at said data storing step for the personal data based on inputted search data, for reading out part images designated by the designation data corresponding to the personal data from said part image storage memory when the personal data which coincide with the inputted search data is found, and for controlling said display unit to display a living thing image formed by assembling said read-out part images.

69. The image display control method according to claim 68, further comprising printing step of printing the living thing image, or the living thing image with the personal data.

70. The image display control method according to claim 68, wherein the personal data indicate any one of name, address, phone number, age, or height corresponding to the living thing image.

71. The image display control method according to claim 68, wherein the living thing image includes not only a human being image but also images of other living things such as animal images and botanical images.

72. The image display control method according to claim 68, wherein the living thing image is an image representing a face or an image representing a whole body.

73. The image display control method according to claim 68, wherein said data storing step comprises storing step of storing at least one of document data and palm line data corresponding to the living thing image, in addition to the personal data and the designation data.

74. The image display control method according to claim 68, further comprising replacement controlling step of replacing at least one part image of the part images of the living thing image with the other part image stored in said part image storage means, and for controlling said display unit to display the living thing image whose part image has been replaced, in order to modify at least a part of the living thing image being displayed on said display unit controlled by said display controlling step.

75. An image display control method for controlling a display unit to display a living thing image formed by assembling a plurality of part images stored in a part image memory, comprising: data storing step of storing designation data for designating the part images of the living thing image being displayed on said display unit, and personal data indicating at least name and phone number relating to the living thing image, wherein the stored designation data and personal data are associated with each other, and display controlling step of searching data stored at said data storing step for the personal data based on inputted search data, for reading out part images designated by the designation data corresponding to the personal data from said part image storage memory when the personal data which coincide with the inputted search data is found, and for controlling said display unit to display a living thing image formed by assembling said read-out part images and the found personal data.

76. An image display control method for controlling a display unit to display a plurality of living thing images each formed by assembling a plurality of part images stored in a part image memory, comprising: storage controlling step of controlling data storage means to store plural sets of designation data for designating the part images of each living thing image, and plural sets of personal data each including name and phone number relating to the plurality of the living thing images, while associating the designation data and the personal data with each other, before the plurality of living thing images are displayed on said display unit.

77. The image display control method according to claim 76, further comprising display controlling step of searching data stored at said data storing step for the personal data based on inputted search data, for reading out part images designated by the designation data corresponding to the personal data from said part image memory when the personal data which coincide with the inputted search data is found, and for controlling said display unit to display a living thing image formed by assembling said read-out part images and the found personal data.

78. The image display control method according to claim 76, further comprising display controlling method of reading out plural sets of part images designated by the plurality of designation data sets corresponding to the plurality of personal data sets stored at said data storing step from said part image memory, and for controlling said display unit to collectively display a plurality of living thing images each of which is formed by assembling the read-out part images.

* * * * *